US012340906B2

United States Patent
Wagner et al.

(10) Patent No.: US 12,340,906 B2
(45) Date of Patent: Jun. 24, 2025

(54) NONINVASIVE METHODS FOR DETECTION OF PULMONARY HYPERTENSION

(71) Applicant: Anumana, Inc., Cambridge, MA (US)

(72) Inventors: Tyler Wagner, Boston, MA (US); Samir Awasthi, Boston, MA (US); Venkataramanan Soundararajan, Andover, MA (US); Murali Aravamudan, Andover, MA (US); Corinne Carpenter, Cambridge, MA (US); Katherine Carlson, Cambridge, MA (US); Itzhak Zachi Attia, Rochester, MA (US); Paul A. Friedman, Rochester, MN (US); Samuel J. Asirvatham, Rochester, MN (US); Suraj Kapa, Rochester, MN (US); Francisco Lopez-Jimenez, Rochester, MN (US); Hilary M. Dubrock, Rochester, MN (US)

(73) Assignee: Anumana, Inc., Cambridge, MA (US)

( * ) Notice: Subject to any disclaimer, the term of this patent is extended or adjusted under 35 U.S.C. 154(b) by 269 days.

(21) Appl. No.: 17/500,287

(22) Filed: Oct. 13, 2021

(65) Prior Publication Data
US 2022/0189634 A1 Jun. 16, 2022

Related U.S. Application Data

(60) Provisional application No. 63/091,715, filed on Oct. 14, 2020.

(51) Int. Cl.
G16H 50/00 (2018.01)
A61B 5/341 (2021.01)
(Continued)

(52) U.S. Cl.
CPC ............ G16H 50/20 (2018.01); A61B 5/341 (2021.01); A61B 5/349 (2021.01); G16H 10/60 (2018.01)

(58) Field of Classification Search
CPC ........ G16H 50/20; G16H 10/60; A61B 5/349; A61B 5/341
See application file for complete search history.

(56) References Cited

U.S. PATENT DOCUMENTS

2019/0354883 A1  11/2019  Aravamudan et al.
2020/0038671 A1   2/2020  Schulhauser et al.
(Continued)

FOREIGN PATENT DOCUMENTS

WO    WO-2022081646 A1 *  4/2022  ............ A61B 5/341

OTHER PUBLICATIONS

Proquest article by Aaron Michael Wenger A Dissertation submitted to the Department of Computer Science and the Committee on graduate studies of Standford University in Partial Fulfillment of the Requirements for the Degree of Doctor of Philosophy (Year: 2012).*

(Continued)

*Primary Examiner* — Raquel Alvarez
(74) *Attorney, Agent, or Firm* — Caldwell Intellectual Property Law

(57) ABSTRACT

Provided herein are methods, systems, and computer program products for the detection of pulmonary hypertension comprising receiving voltage-time data of a plurality of leads of an electrocardiograph of a subject; generating a feature vector from the voltage-time data; providing the feature vector to a pretrained learning system; and receiving from the pretrained learning system an indication of the presence or absence of pulmonary hypertension in the subject.

18 Claims, 20 Drawing Sheets

(51) Int. Cl.
*A61B 5/349* (2021.01)
*G16H 10/60* (2018.01)
*G16H 50/20* (2018.01)

(56) References Cited

U.S. PATENT DOCUMENTS

2020/0205745 A1    7/2020  Khosousi et al.
2022/0093252 A1*  3/2022  Molony ................ G16H 70/60

OTHER PUBLICATIONS

International Search Report and Written Opinion for International Application No. PCT/US2021/054693 dated Jan. 12, 2022.
Geoffrey H Tison et al: "Automated and Interpretable Patient ECG Profiles for Disease Detection, Tracking, and Discovery", arxiv.org, Cornell University Library, 201 Olin Library Cornell University Ithaca, NY 14853, Jul. 6, 2018 (Jul. 6, 2018), XP081244930, * the whole document *.
EP 21 88 0954; Supplementary European Search Report; Date: Sep. 23, 2024.

* cited by examiner

|  | Sentiment + Echo | Sentiment ONLY | Echo ONLY |
|---|---|---|---|
| 10X CV Test Set Accuracy | 0.968 | 0.951 | 0.900 |
| 10X CV Test Set St. Dev. | 0.009 | 0.010 | 0.027 |
| AUC of ROC | 1.00 | 0.99 | 0.97 |

Patient Vector = [% YES, % NO, % MAYBE, % OTHER, PH Sentences / Note, TRV_MIN, TRV_MAX, TRV_STD, TRV_MED, TRV_MEAN, RAP_MIN, RAP_MAX, RAP_STD, RAP_MED, RAP_MEAN]

FIG. 8

On ECGs within 1 month window of diagnosis

| Metric / Threshold | Patient Wise | Age Gender Wise |
|---|---|---|
| AUC | 0.9436 | 0.9397 |
| Sensitivity | 0.8745 | 0.8702 |
| Specificity | 0.8743 | 0.870 |
| OddsRatio | 47.5794 | 45.3278 |
| PPV | 0.5726 | 0.6284 |
| NPV | 0.9726 | 0.9640 |
| J Threshold | 0.0861 | 0.1264 |

* Odds Ratio = ratio of the odds of testing positive if the patient has PH relative to the odds of testing positive if the patient doesn't have PH, i.e. OR = (TP/FN) / (FP/TN)
* J Threshold is maximizing arithmetic mean of Sensitivity and Specificity

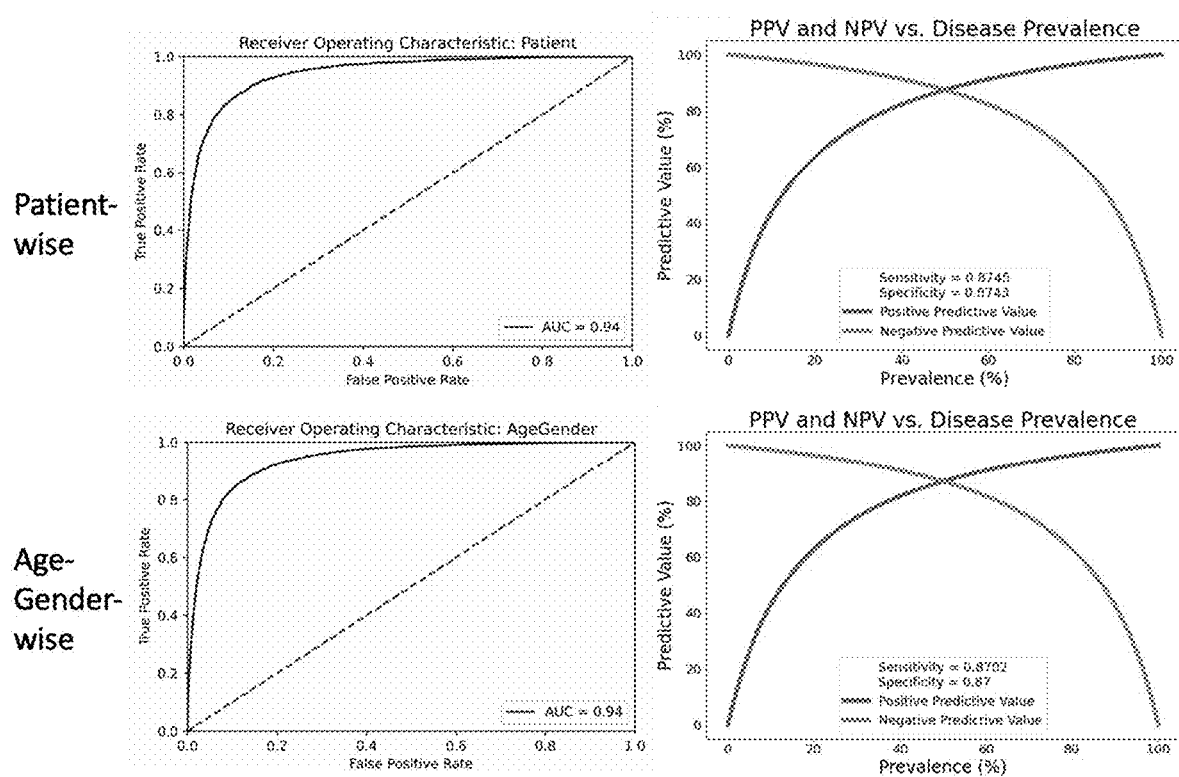

FIG. 9

On ECGs 6-18 months prior to diagnosis

| Metric / Threshold | Patient Wise | Age Gender Wise |
|---|---|---|
| AUC | 0.9023 | 0.8961 |
| Sensitivity | 0.830 | 0.8205 |
| Specificity | 0.8308 | 0.8198 |
| OddsRatio | 23.9908 | 20.6087 |
| PPV | 0.2119 | 0.5306 |
| NPV | 0.9889 | 0.9480 |
| J Threshold | 0.0528 | 0.0713 |

- Odds Ratio = ratio of the odds of testing positive if the patient has PH relative to the odds of testing positive if the patient doesn't have PH, i.e. OR = (TP/FN) / (FP/TN)
- J Threshold is maximizing arithmetic mean of Sensitivity and Specificity

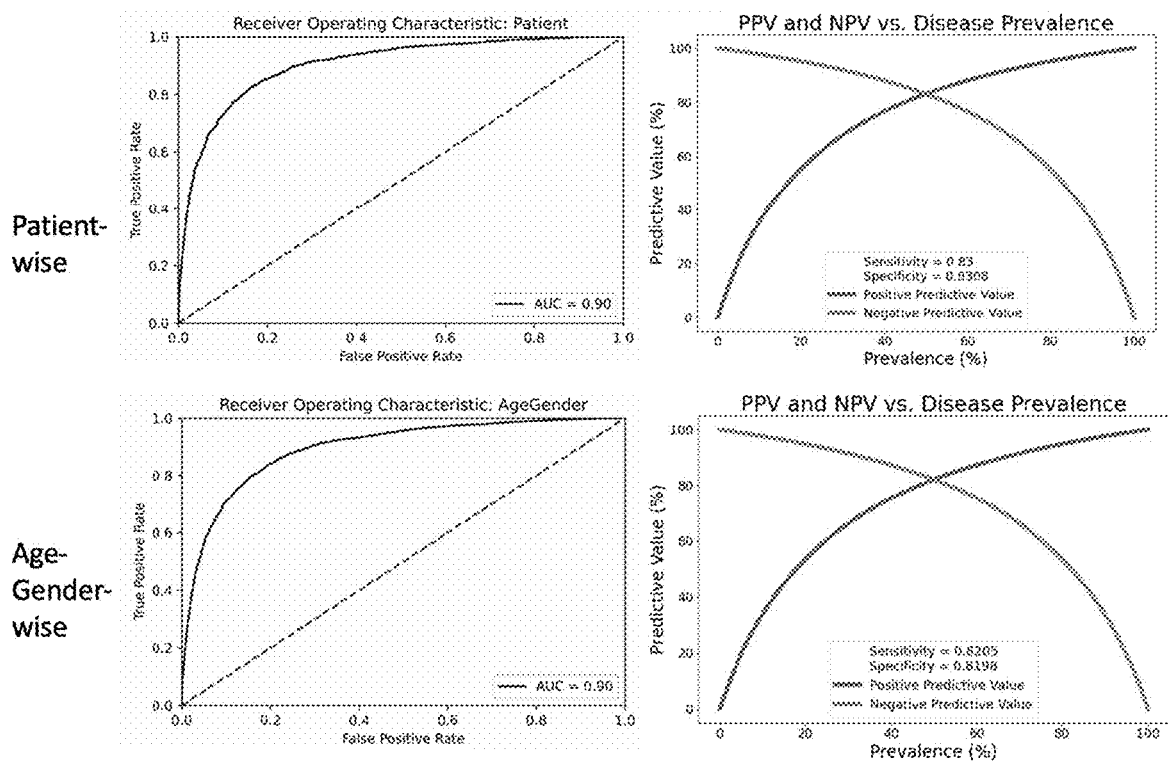

Patient-wise

Age-Gender-wise

FIG. 13A

Expression of KCNK3 By Cell Type

| Cell Type | % Cells Expressing | Obs/Exp Ratio | Supporting Studies | Cohen's D | Scaled Composite Score |
|---|---|---|---|---|---|
| Delta Cells | 51.35 | 63.67 | 2 of 2 | 0.87 | 1 |
| Alpha Cell | 39.31 | 77.13 | 2 of 3 | 0.95 | 0.88 |
| Gamma Cell | 45.87 | 57.8 | 2 of 2 | 0.78 | 0.82 |
| Beta Cell | 35.7 | 59.6 | 2 of 3 | 0.87 | 0.76 |
| Bipolar Neurons | 15.12 | 20.7 | 1 of 1 | 0.48 | 0.63 |

Expression of KCNK3 By Tissue

| Tissue | % Cells Expressing | Obs/Exp Ratio | Supporting Studies | Cohen's D | Scaled Composite Score |
|---|---|---|---|---|---|
| Pancreas | 19.1 | 34.53 | 2 of 3 | 0.54 | 1 |
| Adrenal Gland | 3.36 | 5.7 | 1 of 1 | 0.24 | 0.52 |
| Cervix | 1.75 | 3.76 | 1 of 1 | 0.18 | 0.32 |
| Brain | 1.38 | 1.75 | 1 of 1 | 0.11 | 0.14 |
| Brain Prefrontal Cortex | 1.54 | 1.78 | 1 of 1 | 0.12 | 0.12 |

FIG. 13B

Expression of KCNA5 By Cell Type

| Cell Type | % Cells Expressing | Obs/Exp Ratio | Supporting Studies | Cohen's D | Scaled Composite Score |
|---|---|---|---|---|---|
| Bipolar Neurons | 29.06 | 53.94 | 1 of 1 | 0.69 | 1 |
| Alpha Cell | 27.69 | 72.13 | 3 of 3 | 0.62 | 0.88 |
| Vascular Smooth Muscle Cells | 16.5 | 16.5 | 1 of 1 | 0.45 | 0.71 |
| Smooth Muscle Cells | 6.84 | 11.71 | 22 of 27 | 0.22 | 0.71 |
| Gamma Cell | 36.91 | 79 | 2 of 2 | 0.66 | 0.65 |

1-5 of 340

Expression of KCNA5 By Tissue

| Tissue | % Cells Expressing | Obs/Exp Ratio | Supporting Studies | Cohen's D | Scaled Composite Score |
|---|---|---|---|---|---|
| Heart | 3.65 | 14.27 | 2 of 2 | 0.13 | 1 |
| Retina | 2.77 | 8.59 | 2 of 2 | 0.23 | 0.87 |
| Muscle | 2.55 | 6.36 | 1 of 1 | 0.23 | 0.74 |
| Pancreas | 8.77 | 20.98 | 2 of 3 | 0.25 | 0.6 |
| Uterus | 0.83 | 2.52 | 1 of 1 | 0.13 | 0.28 |

NONINVASIVE METHODS FOR DETECTION OF PULMONARY HYPERTENSION

CROSS-REFERENCE TO RELATED APPLICATIONS

This application claims benefit of U.S. Provisional Application No. 63/091,715, filed Oct. 14, 2020, which is hereby incorporated by reference in its entirety.

BACKGROUND

Embodiments of the present disclosure relate to methods for the diagnosis and treatment of pulmonary hypertension. Pulmonary hypertension (PH) is a life-threatening disease estimated to affect 1% of the global population and up to 10% of patients over 65 years of age. The timely diagnosis of PH is imperative not only for effective therapeutic intervention but also to amplify the odds of survival. Multiple studies suggest that earlier diagnosis, by even a few months, can lead to dramatic increases in quality of life and lifespan extension. However, the symptoms of PH are non-specific and very similar to the symptoms seen in other common diseases, including asthma, chronic obstructive pulmonary disease (COPD), and heart failure. This makes suspicion of PH low within ambulatory care settings, thus timely referral to pulmonologists or cardiologists who can confirm diagnosis is critical. Currently, delay in diagnosis can occur with an average time of 2.5 years (from onset of symptoms to diagnosis) and up to 4 years in some cases, primarily due to delayed referral to the appropriate specialists. Indeed, because the gold standard for the definitive diagnosis of PH is right heart catheterization (RHC), an invasive procedure that entails non-negligible risks, physicians often hesitate to proceed until all other diseases have been sequentially ruled out. Thus, there is a great need for new and improved methods, e.g., diagnostic methods, for early and accurate detection of PH. Accordingly, embodiments of the invention disclosed herein include algorithms applied to electrocardiograms (ECGs), a non-invasive procedure, in the diagnostic workup of PH for the detection of PH and stratification of patients based on the risk of PH, allowing earlier diagnosis and intervention.

BRIEF SUMMARY

According to embodiments of the present disclosure, methods of and computer program products for the detection of pulmonary hypertension are provided.

In some aspects of the invention, disclosed herein are methods comprising receiving voltage-time data of a subject, the voltage-time data comprising voltage data of a plurality of leads of an electrocardiograph; generating a feature vector from the voltage-time data; providing the feature vector to a pretrained learning system; and receiving from the pretrained learning system an indication of the presence or absence of pulmonary hypertension in the subject.

Aspects of the invention, as disclosed herein, also include a system comprising: an electrocardiograph comprising a plurality of leads; a computing node comprising a computer readable storage medium having program instructions embodied therewith, the program instructions executable by a processor of the computing node to cause the processor to perform a method comprising: receiving voltage-time data of a subject from the echocardiograph, the voltage-time data comprising voltage data of the plurality of leads; generating a feature vector from the voltage-time data; providing the feature vector to a pretrained learning system; and receiving from the pretrained learning system an indication of the presence or absence of pulmonary hypertension in the subject.

In certain aspects of the invention, disclosed herein is a computer program product for detection of pulmonary hypertension, the computer program product comprising a computer readable storage medium having program instructions embodied therewith, the program instructions executable by a processor to cause the processor to perform a method comprising: receiving voltage-time data of a subject from the echocardiograph, the voltage-time data comprising voltage data of the plurality of leads; generating a feature vector from the voltage-time data; providing the feature vector to a pretrained learning system; and receiving from the pretrained learning system an indication of the presence or absence of pulmonary hypertension in the subject.

BRIEF DESCRIPTION OF THE SEVERAL VIEWS OF THE DRAWINGS

FIG. 8 depicts the Cohort 3 diagnostic model on ECGs from the diagnostic window.

FIG. 9 depicts the Cohort 3 diagnostic model on ECGs from the pre-emptive window.

FIG. 13A-B presents the output of the nferX Single Cell application, which showed that both KCNK3 (A, upper) and KCNA5 (B, upper) are expressed strongly in neuronal and cardiac cell types, respectively. Notably, KNCK3 expression is also observed in cardiac cell types at lower expression levels (not shown).

FIG. 14 presents the output of the nferX Signals application, which identified numerous sources of literature evidence that suggest that mutations in both KCNK3 (left), also called TASK1, and KCNA5 (right) impact cardiac electrophysiology and may therefore be detectable in the electrocardiogram.

DETAILED DESCRIPTION

Figure 1:
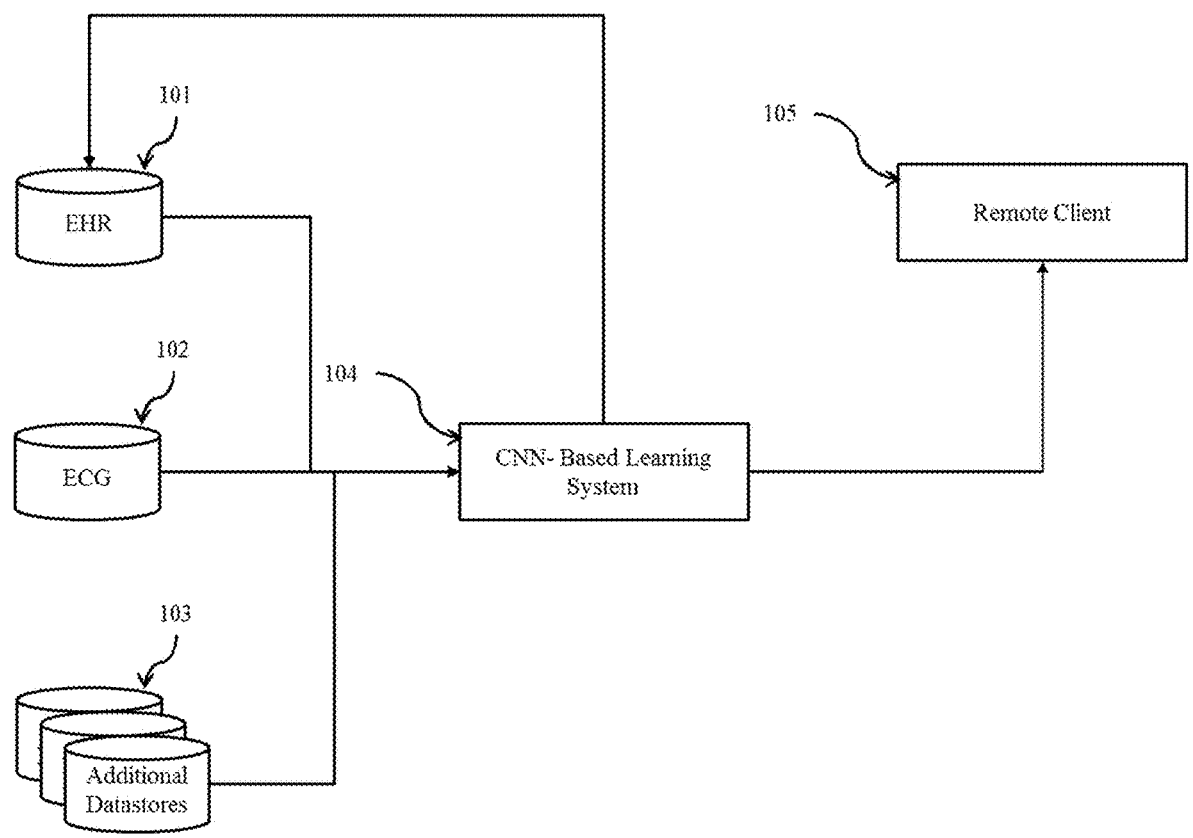
FIG. 1 is a schematic view of a system for detecting pulmonary hypertension according to embodiments of the present disclosure.

Convolutional neural networks offer a comprehensive approach to analyzing and interpreting the vast amount of data generated in a single ECG. Algorithms were developed using retrospective Mayo Clinic, patient-level data; including ECGs, procedural measurements, physician notes, and patient demographics for the purpose of screening patients for PH. In order to distinguish between PH and non-PH patients for model training, each ECG was paired with either an RHC or an echocardiogram. Measurements derived from these procedures were used to define the cohorts. This yielded 65,994 unique patients (11,238 PH and 54,756 non-PH) of which 48% were used in model training, 12% held-out for preliminary validation, and a final 40% held-out for testing.

All models used voltage-time information from 12-lead ECGs as inputs. Modeling techniques explored included convolutional neural networks with differing structures such as using all 12 leads as a single input, groups of 3 leads as separate inputs, each lead converted to spectrogram, and combinations of these methods. Additionally, two distinct preliminary models were created, one in which the ECG was performed within a month of the patient's diagnosis (diagnostic model) and another in which the ECG was performed 6 to 18 months prior to the diagnosis date (pre-emptive model). Based on relative performance at that time, the preliminary diagnostic model was selected for further development.

The best performing preliminary diagnostic model was a convolutional neural network with residual connections incorporating the 12-lead single input. The updated diagnostic model obtained an area under the curve (AUC) of 0.94 on the diagnostic validation and test sets, and was able to distinguish PH 6 to 18 months prior to diagnosis with an AUC of 0.90 on the validation and test sets. Finally, ECGs taken 3-5 years prior to diagnosis did not exhibit a significant decrease in performance, with AUCs above 0.8466. Ultimately, these results show a strong signal within ECGs for detecting PH and could be implemented in ECG machines in primary and secondary care settings to accelerate patient diagnosis and intervention. Additionally, the disease also comprises an underlying genetic component, which is supported by the detection of these diagnostic signals 3-5 years prior to diagnosis. The methods disclosed herein may be coupled with a genetic panel to provide further specificity and sensitivity. Similarly, such methods may be used with genetic panels to detect novel biomarkers of disease.

Accordingly, in some aspects of the invention, disclosed herein are methods comprising receiving voltage-time data of a subject, the voltage-time data comprising voltage data of a plurality of leads of an electrocardiograph; generating a feature vector from the voltage-time data; providing the feature vector to a pretrained learning system; and receiving from the pretrained learning system an indication of the presence or absence of pulmonary hypertension in the subject. Generating the feature vector may comprise generating a spectrogram based on the voltage data of the plurality of leads. In some embodiments generating the feature vector comprises grouping the voltage data of the plurality of leads into a plurality of subsets.

In some embodiments, such methods further comprise receiving demographic information of the subject, wherein generating the feature vector comprises adding the demographic information to the feature vector. In some such embodiments, the learning system comprises a convolutional neural network. Such convolutional neural networks may comprise at least one residual connection.

In some embodiments the voltage-time data of a subject is received from an electrocardiograph. In further embodiments, the voltage-time data of a subject is received from an electronic medical record.

In some embodiments, the method further comprises providing the indication to an electronic health record system for storage in a health record associated with the subject. In some embodiments, the method further comprises providing the indication to a computing node for display to a user.

With reference now to FIG. 1, a system for detecting pulmonary hypertension is illustrated according to embodiments of the present disclosure. As outlined above, in various embodiments, patient information, including electrocardiogram (ECG) data, is provided to a learning system in order to determine the presence of pulmonary hypertension. Thus, aspects of the invention, as disclosed herein, also include a system comprising: an electrocardiograph comprising a plurality of leads; a computing node comprising a computer readable storage medium having program instructions embodied therewith, the program instructions executable by a processor of the computing node to cause the processor to perform a method comprising: receiving voltage-time data of a subject from the echocardiograph, the voltage-time data comprising voltage data of the plurality of leads; generating a feature vector from the voltage-time data; providing the feature vector to a pretrained learning system; and receiving from the pretrained learning system an indication of the presence or absence of pulmonary hypertension in the subject. Generating the feature vector may comprise generating a spectrogram based on the voltage data of the plurality of leads. In some embodiments generating the feature vector comprises grouping the voltage data of the plurality of leads into a plurality of subsets.

In some embodiments, such systems further comprise receiving demographic information of the subject, wherein generating the feature vector comprises adding the demographic information to the feature vector. In some such embodiments, the learning system comprises a convolutional neural network. Such convolutional neural networks may comprise at least one residual connection.

In some embodiments the voltage-time data of a subject is received from an electrocardiograph. In further embodiments, the voltage-time data of a subject is received from an electronic medical record.

In some embodiments, the system further comprises providing the indication to an electronic health record system for storage in a health record associated with the subject. In some embodiments, the system further comprises providing the indication to a computing node for display to a user.

Patient data may be received from electronic health record (EHR) 101. An electronic health record (EHR), or electronic medical record (EMR), may refer to the systematized collection of patient and population electronically-stored health information in a digital format. These records can be shared across different health care settings. Records may be shared through network-connected, enterprise-wide information systems or other information networks and exchanges. EHRs may include a range of data, including demographics, medical history, medication and allergies, immunization status, laboratory test results, radiology images, vital signs, personal statistics like age and weight, and billing information. EHR systems may be designed to store data and capture the state of a patient across time. In this way, the need to track down a patient's previous paper medical records is eliminated.

Electrocardiogram (ECG) data may be received directly from an electrocardiography device 102. In an exemplary 12-lead ECG, ten electrodes are placed on the patient's limbs and on the surface of the chest. The overall magnitude of the heart's electrical potential is then measured from twelve different angles (leads) and is recorded over a period of time (usually ten seconds). In this way, the overall magnitude and direction of the heart's electrical depolarization is captured at each moment throughout the cardiac cycle.

Additional datastores 103, may include further patient information as set out herein. Suitable datastores include databases, flat files, and other structures known in the art.

It will be appreciated that ECG data may be stored in an EHR for later retrieval. It will also be appreciated that ECG data may be cached, rather than delivered directly to a learning system for further processing.

Learning system 104 receives patient information from one or more of EHR 101, ECG 102, and additional datastores 103. As set out above, in some embodiments, the learning system comprises a convolutional neural network. In various embodiments, the input to the convolutional neural network comprises voltage-time information an ECG, which in some embodiments is paired with additional patient information such as demographics or genetic information.

Learning system 104 may be pretrained using suitable population data as set out in the examples in order to produce an indication of the presence or absence of pulmonary hypertension. In some embodiments, the indication is binary. In some embodiments, the indication is a probability value, indicating the likelihood of pulmonary hypertension given the input patient data.

In some embodiments, learning system 104 provides the indication of pulmonary hypertension for storage as part of an EHR. In this way, a computer-aided diagnosis is provided, which may be referred to by a clinician. In some embodiments, learning system 104 provides the indication of pulmonary hypertension to a remote client 105. For example, a remote client may be a health app, a cloud service, or another consumer of diagnostic data. In some embodiments, the learning system 104 is integrated into an ECG machine for immediate feedback to a user during testing.

In some embodiments, a feature vector is provided to a learning system. Based on the input features, the learning system generates one or more outputs. In some embodiments, the output of the learning system is a feature vector.

In some embodiments, the learning system comprises a SVM. In other embodiments, the learning system comprises an artificial neural network. In some embodiments, the learning system is pre-trained using training data. In some embodiments training data is retrospective data. In some embodiments, the retrospective data is stored in a data store. In some embodiments, the learning system may be additionally trained through manual curation of previously generated outputs.

In some embodiments, the learning system, is a trained classifier. In some embodiments, the trained classifier is a random decision forest. However, it will be appreciated that a variety of other classifiers are suitable for use according to the present disclosure, including linear classifiers, support vector machines (SVM), or neural networks such as recurrent neural networks (RNN).

Suitable artificial neural networks include but are not limited to a feedforward neural network, a radial basis function network, a self-organizing map, learning vector quantization, a recurrent neural network, a Hopfield network, a Boltzmann machine, an echo state network, long short term memory, a bi-directional recurrent neural network, a hierarchical recurrent neural network, a stochastic neural network, a modular neural network, an associative neural network, a deep neural network, a deep belief network, a convolutional neural networks, a convolutional deep belief network, a large memory storage and retrieval neural network, a deep Boltzmann machine, a deep stacking network, a tensor deep stacking network, a spike and slab restricted Boltzmann machine, a compound hierarchical-deep model, a deep coding network, a multilayer kernel machine, or a deep Q-network.

In machine learning, a convolutional neural network (CNN) is a class of feed-forward artificial neural networks applicable to analyzing visual imagery and other natural signals. A CNN consists of an input and an output layer, as well as multiple hidden layers. The hidden layers of a CNN typically consist of convolutional layers, pooling layers, fully connected layers and normalization layers. Convolutional layers apply a convolution operation to the input, passing the result to the next layer. The convolution emulates the response of an individual neuron to stimuli. Each convolutional neuron processes data only for its receptive field.

A convolution operation, allows a reduction in free parameters as compared to a fully connected feed forward network. In particular, tiling a given kernel allows a fixed number of parameters to be learned irrespective of image size. This likewise reduces the memory footprint for a given network.

A convolutional layer's parameters consist of a set of learnable filters (or kernels), which have a small receptive field, but extend through the full depth of the input volume. During the forward pass, each filter is convolved across the width and height of the input volume, computing the dot product between the entries of the filter and the input and producing a 2-dimensional activation map of that filter. As a result, the network learns filters that activate when it detects some specific type of feature at some spatial position in the input.

In an exemplary convolution, a kernel comprises a plurality of weights $w_1 \ldots w_9$. It will be appreciated that the sizes provided here are merely exemplary, and that any kernel dimension may be used as described herein. The kernel is applied to each tile of an input (e.g., an image). The result of each tile is an element of a feature map. It will be appreciated that a plurality of kernels may be applied to the same input in order to generate multiple feature maps.

Stacking the feature maps for all kernels forms a full output volume of the convolution layer. Every entry in the output volume can thus also be interpreted as an output of a neuron that looks at a small region in the input and shares parameters with neurons in the same feature map.

Convolutional neural networks may be implemented in various hardware, including hardware CNN accelerators and GPUs.

Figure 2:
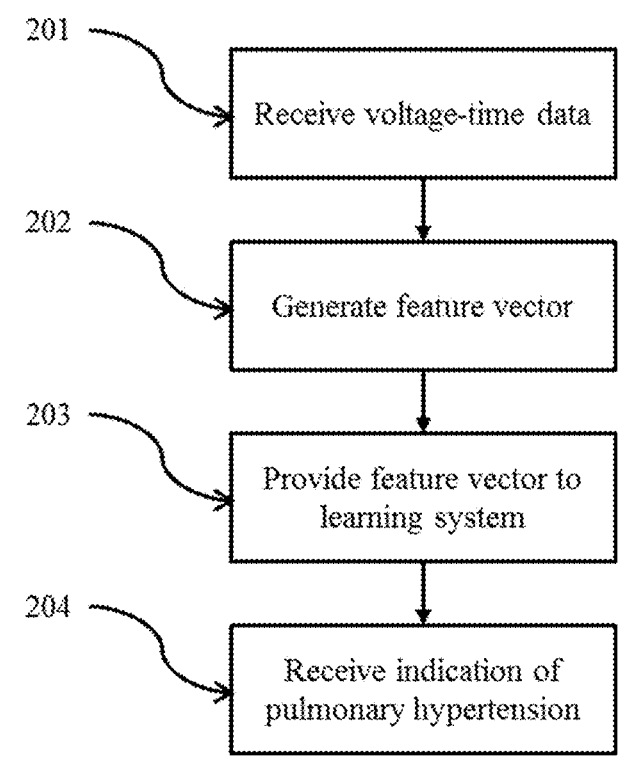
FIG. 2 is a flowchart illustrating a method of detecting pulmonary hypertension according to embodiments of the present disclosure.

Referring now to FIG. 2, a flowchart is provided illustrating a method of detecting pulmonary hypertension according to embodiments of the present disclosure. At 201, voltage-time data of a subject is received. The voltage-time data comprises voltage data of a plurality of leads of an electrocardiograph. At 202, a feature vector is generated from the voltage-time data. At 203, the feature vector is provided to a pretrained learning system. At 204, an indication of the presence or absence of pulmonary hypertension in the subject is received from the pretrained learning system.

Figure 3:
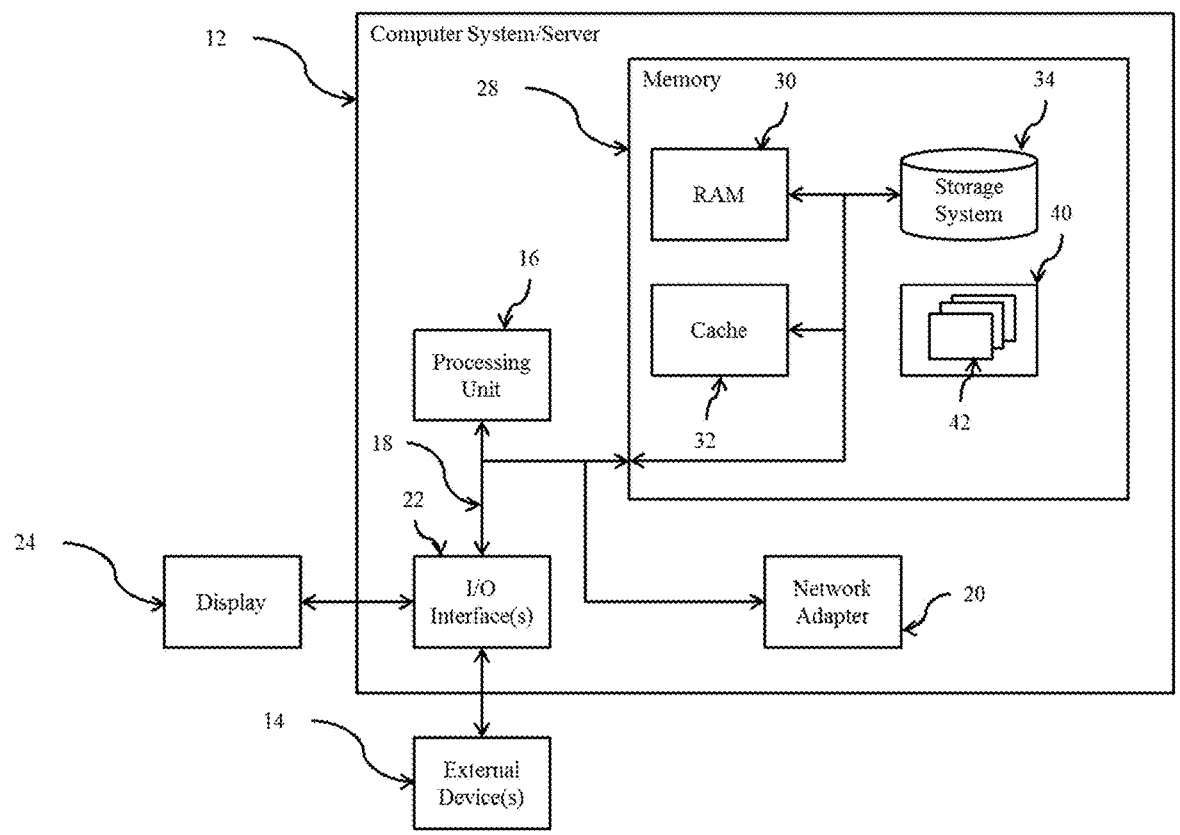
FIG. 3 depicts a computing node according to an embodiment of the present disclosure.

Referring now to FIG. 3, a schematic of an example of a computing node is shown. Computing node 10 is only one example of a suitable computing node and is not intended to suggest any limitation as to the scope of use or functionality of embodiments described herein. Regardless, computing node 10 is capable of being implemented and/or performing any of the functionality set forth hereinabove.

In computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 3, computer system/server 12 in computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, Peripheral Component Interconnect (PCI) bus, Peripheral Component Interconnect Express (PCIe), and Advanced Microcontroller Bus Architecture (AMBA).

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the disclosure.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

The present disclosure may be embodied as a system, a method, and/or a computer program product. For example, in some aspects or the invention, provided herein is a computer program product for detection of pulmonary hypertension, the computer program product comprising a computer readable storage medium having program instructions embodied therewith, the program instructions executable by a processor to cause the processor to perform a method comprising: receiving voltage-time data of a subject from the echocardiograph, the voltage-time data comprising voltage data of the plurality of leads; generating a feature vector from the voltage-time data; providing the feature vector to a pretrained learning system; and receiving from the pretrained learning system an indication of the presence or absence of pulmonary hypertension in the subject. Generating the feature vector may comprise generating a spectrogram based on the voltage data of the plurality of leads. In some embodiments generating the feature vector comprises grouping the voltage data of the plurality of leads into a plurality of subsets.

In some embodiments, such computer program products further comprise receiving demographic information of the subject, wherein generating the feature vector comprises adding the demographic information to the feature vector. In some such embodiments, the learning system comprises a convolutional neural network. Such convolutional neural networks may comprise at least one residual connection.

In some embodiments the voltage-time data of a subject is received from an electrocardiograph. In further embodiments, the voltage-time data of a subject is received from an electronic medical record.

In some embodiments, the computer program product further comprises providing the indication to an electronic health record system for storage in a health record associated with the subject. In some embodiments, the system further comprises providing the indication to a computing node for display to a user.

The computer program product provided herein may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

EXAMPLES

Example 1: Cohort Identification & Augmented Curation

A diverse set of cohorts were generated for preliminary model development using a combination of mean pulmonary arterial pressure (mPAP) measured during RHC and tricuspid regurgitation velocity (TRV) measured during echocardiogram (Table 1). RHC is the gold standard for PH diagnosis, with an mPAP greater than or equal to 21 mmHg denoting PH (recently lowered from the previous threshold of 25 mmHg). TRV measurements are less conclusive, i.e., while TRV less than or equal to 2.8 m/s indicates the absence of PH and TRV greater than or equal to 3.4 m/s indicates its presence, there is an intermediate range for which diagnosis is inconclusive using TRV alone and other measured must be considered.

TABLE 1

Cohorts used for preliminary model development

| Cohort | Positive | Unique Patients | Negative | Unique Patients |
|---|---|---|---|---|
| 1 | mPAP ≥25 mmHg | 11215 | mPAP <21 mmHg | 2293 |
| 2 | mPAP ≥21 mmHg | 12827 | mPAP <21 mmHg | 2293 |
| 3 | mPAP ≥25 mmHg | 11215 | mPAP <21 mmHg + TRV ≤2.8 m/s | 50768 |
| 4 | mPAP ≥21 mmHg | 12827 | mPAP <21 mmHg + TRV ≤2.8 m/s | 50768 |
| 5 | TRV ≥3.4 m/s | 15515 | TRV ≤2.8 m/s | 49614 |
| 6 | TRV >2.8 m/s | 39238 | TRV ≤2.8 m/s | 49614 |
| 7 | Echo + Clinical Notes Positive | 5994 | Echo + Clinical Notes Negative | 56835 |
| 8 | mPAP ≥25 mmHg | 11215 | mPAP <21 mmHg + TRV ≤2.6 m/s | 41804 |
| 9 | mPAP ≥21 mmHg | 12827 | mPAP <21 mmHg + TRV ≤2.6 m/s | 41804 |
| 10 | TRV ≥3.4 m/s | 15515 | TRV ≤2.6 m/s | 40263 |
| 11 | TRV >2.8 m/s | 39238 | TRV ≤2.6 m/s | 40263 |
| 12 | mPAP >20 mmHg + TRV >3.4 m/s | 19422 | mPAP ≤20 mmHg + TRV <2.8 m/s | 42144 |

Additionally, one cohort was generated using diagnosis extracted from the clinical notes, coupled with echo measurements to test the capabilities of augmented curation (Cohort 7). This cohort was generated using a subset of patients with echocardiogram measurements, which accounts for the lower number of PH patients. As a first step toward this end, Mayo physicians provided a positive control cohort of 1,630 patients, hereafter referred to as the Mayo PH Cohort. To expand this cohort an additional 19,504 patients that contained the term "pulmonary hypertension" were identified within their notes, hereafter referred to as the Potential PH Cohort. A BERT model was trained to classify the sentiment regarding a PH diagnosis. This model was used to distinguish between true positive and negative patients in the Mayo and Potential PH Cohorts, and how such a model could scale to additional diseases and features.

Example 2: Training a BERT Model for Diagnoses

As a first step toward creating a BERT model for diagnosis, the Nference® Signals application was used to determine the top 250 phenotypes most closely associated to "pulmonary hypertension" and sentences from the Mayo corpus of clinical notes were extracted for these phenotypes. Sentences were manually classified by MD- and PhD-level scientists at nference into categories, e.g., positive (YES), negative (NO), suspected (MAYBE), and alternate context (OTHER), with examples shown in Table 2.

TABLE 2

| Manual classifications | |
|---|---|
| Positive diagnosis (YES) | Negative diagnosis (NO) |
| "In regard to Ms. LNAME's history of atrial fibrillation, she reports that she had occasional short episodes of a rapid rate that lasts a minute" "He has severe tricuspid regurgitation due to a partial flail tricuspid leaflet and a history of anemia." | "She has no history of chronic lung disease, rheumatic fever, or endocarditis." "Although her right ventricle is compromised she is quite well compensated hemodynamically without evidence of right ventricular failure." |
| Suspected Diagnosis (MAYBE) | Alternate Context (OTHER) |
| "However, this could also be due to interstitial lung diseases such as sarcoidosis, hypersensitivity pneumonitis, or Langerhans cell histocytosis." "Because of the swelling I wonder about the possibility of cor pulmonale and underlying pulmonary hypertension." | "I have also sent him a copy of our recent paper on smoking-related interstitial lung diseases." "She has no family history of lung fibrosis or other lung diseases." |

Optionally, additional categories may be added to this training set to support increased model granularity, e.g., separating out family history and/or disease risk resulting from medication (both encompassed by OTHER as exemplified above).

A Deep Model Builder application was developed for sentence tagging, with a user interface that improved efficiency while also tracking the changes made across multiple users. The first model was generated on 11,433 sentences and had on overall accuracy of 0.85, defined as the fraction of labels the model correctly predicted over the total sentences. The Deep Model Builder not only enabled the user to review tagged sentences that the model classified incorrectly but could also be used to run the model on an untagged set of sentences, again improving downstream efficiency of the now "augmented curation". As shown in Table 3, with multiple cycles of augmented curation, the accuracy of the model improved from 0.85 to 0.936.

TABLE 3

| Improved model accuracy | | | |
|---|---|---|---|
| 11433 Total Sentences 7409 tagged as YES 1328 tagged as NO 1469 tagged as MAYBE 1195 tagged as OTHER Using all classification labels Accuracy: 0.85 | | | |
| Label | Precision | Recall | F1-Score |
| Other | 0.67 | 0.64 | 0.66 |
| Maybe | 0.65 | 0.61 | 0.63 |
| No | 0.79 | 0.89 | 0.84 |
| Yes | 0.93 | 0.93 | 0.93 |
| 15,121 Total Sentences 9615 tagged as YES 1724 tagged as NO 1930 tagged as MAYBE 1852 tagged as OTHER Using all classification labels Accuracy: 0.91 | | | |
| Label | Precision | Recall | F1-Score |
| Other | 0.81 | 0.75 | 0.78 |
| Maybe | 0.73 | 0.78 | 0.76 |
| No | 0.88 | 0.93 | 0.91 |
| Yes | 0.96 | 0.95 | 0.96 |

TABLE 3-continued

| Improved model accuracy | | | |
|---|---|---|---|
| 18,490 Total Sentences 11,505 tagged as YES 2265 tagged as NO 2235 tagged as MAYBE 2485 tagged as OTHER Using all classification labels Accuracy: 0.936 | | | |
| Label | Precision | Recall | F1-Score |
| Other | 0.81 | 0.91 | 0.86 |
| Maybe | 0.87 | 0.83 | 0.85 |
| No | 0.97 | 0.95 | 0.96 |
| Yes | 0.97 | 0.96 | 0.96 |

Because the aforementioned model was trained on 250 different PH-related phenotypes, the sentences used to train this model were primarily discussing diseases related to cardiology, pulmonology, and metabolic disorders. Given the breadth of the phenotypes already captured by the model, it suggests the model is robust enough to scale to additional therapeutic areas, ranging from COVID-19 to oncology, with minimal retraining (~1000-3000 sentences). Some areas require additional curation to capture specific language or context in that particular field.

To extract the context around a new feature or more specific association, a new model would need to be trained. This is where the augmented curation becomes critical, as it enables the flexibility to create a specific, refined model for any use case. Other methods that structure textual data must predefine the fields needed for manual curation and thus cannot match the speed with which the disclosed method can train a new model for any feature of interest.

Example 3: Using the Diagnosis Model for Cohort Selection

Figure 4:
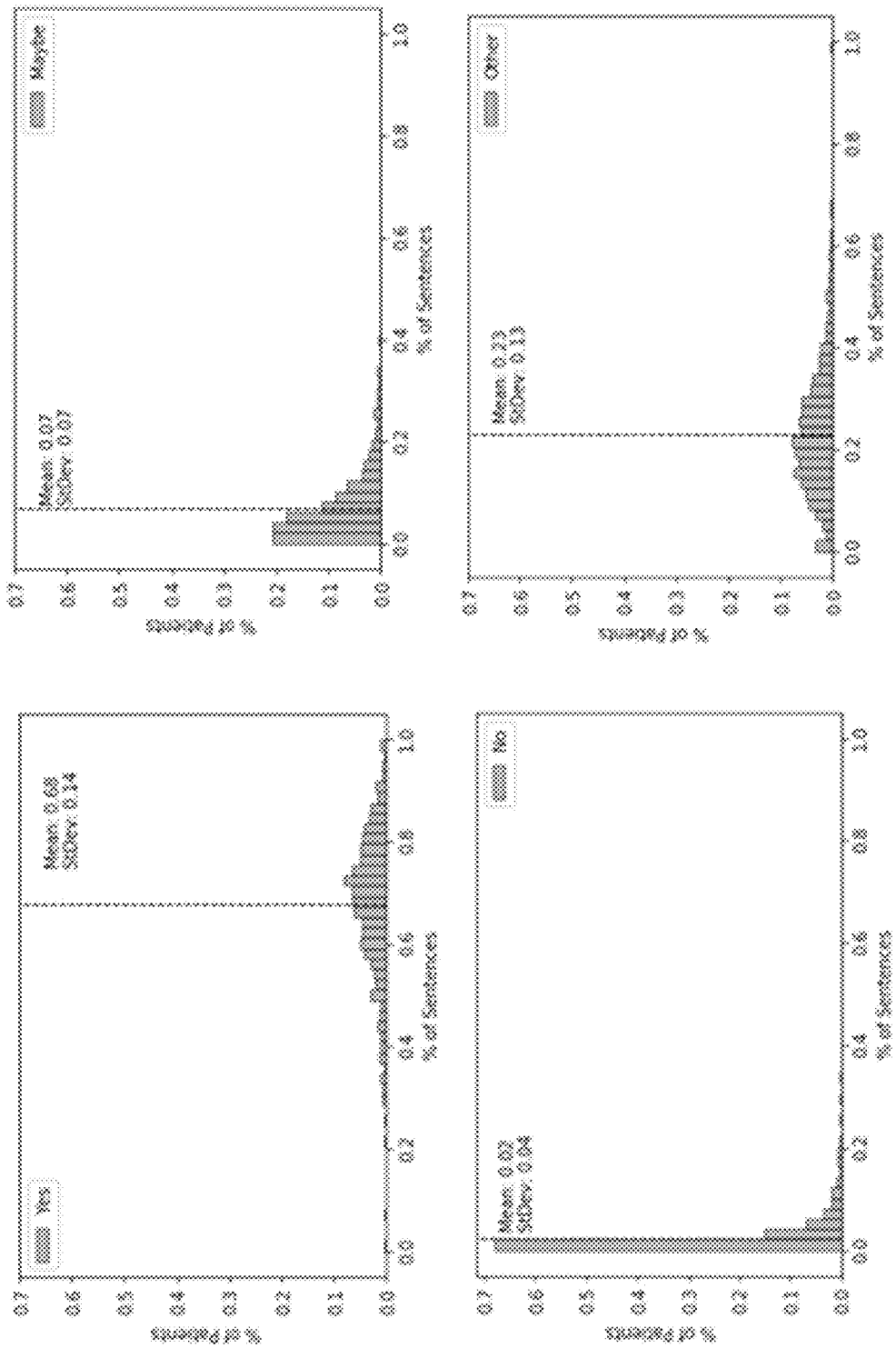
FIG. 4 illustrates the distribution of sentence sentiment for the Mayo PH cohort (positive control), wherein approximately 180,000 sentences in connection with the patients, containing the term "pulmonary hypertension", were classified by the model.

Before running the BERT model on the Potential PH Cohort to identify additional PH patients, it was run on the Mayo PH Cohort to assess the distribution of sentence sentiment for a positive control. Here, approximately 180,000 sentences for these patients containing the term "pulmonary hypertension" were classified by the model. As shown in FIG. 4, on average 68% of sentences were classified as YES sentiment, only 2% as NO, 7% as MAYBE, and 23% as OTHER, an excellent validation of our model and positive cohort.

Figure 5:
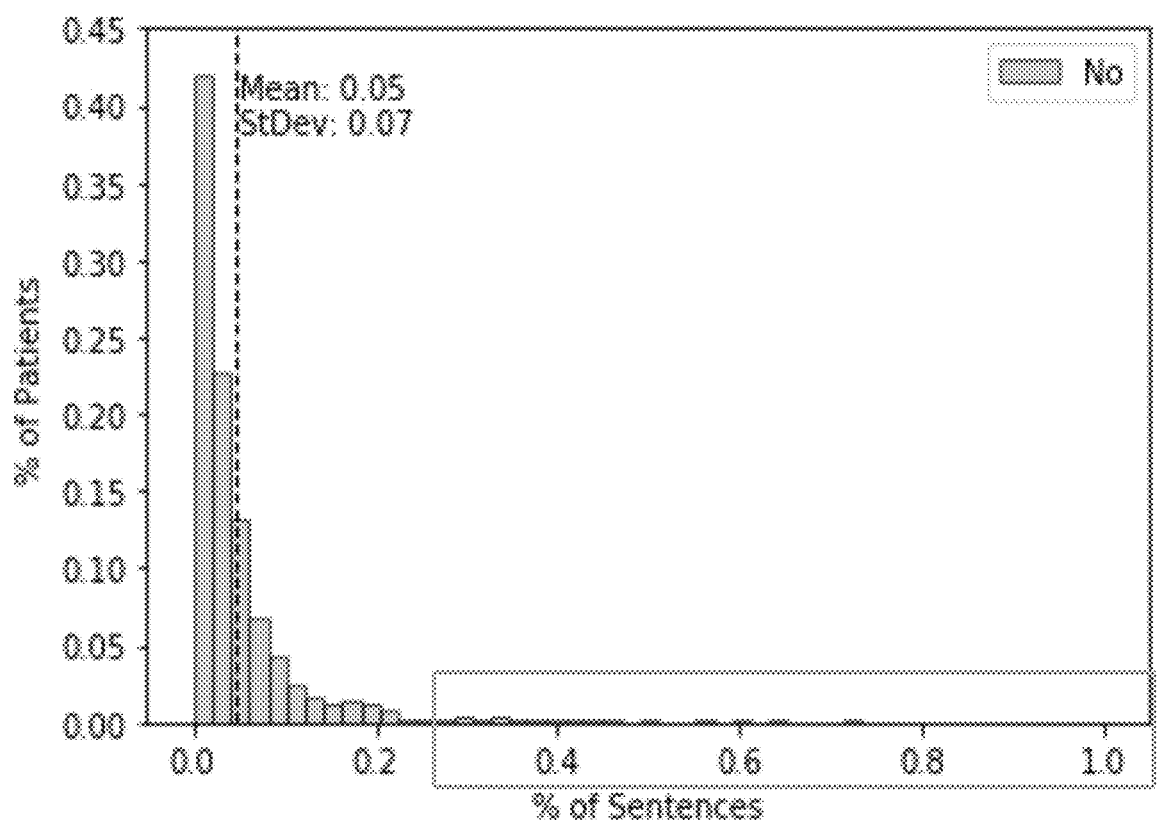
FIG. 5 depicts the output of the sentiment analysis as used to identify patients in the Mayo PH Cohort that did not have PH according to their clinical notes.

The sentiment analysis shown above was also used to identify patients in the Mayo PH Cohort that did not have PH according to their clinical notes. Of the 1,630 patients with clinical notes that were provided, sentiment analysis and subsequent manual review identified 35 patients in this cohort that did not have PH. An example of this semi-automated workflow is shown in FIG. 5. Here, the distribution contains PH negative patients, resulting in a longer tail for the NO classification. For the 25 patients in this particular tail, the nference applications built within the Mayo environment were used to examine each mention of "pulmonary hypertension" in these patients' notes, resulting in 7 patients with PH, 2 with suspected PH, and 16 without PH. The remaining 19 patients within this cohort without PH were identified in a previous iteration. Removing these 35 patients, representing over 2% of the Mayo PH Cohort, could prove significant for model performance.

Figure 6:
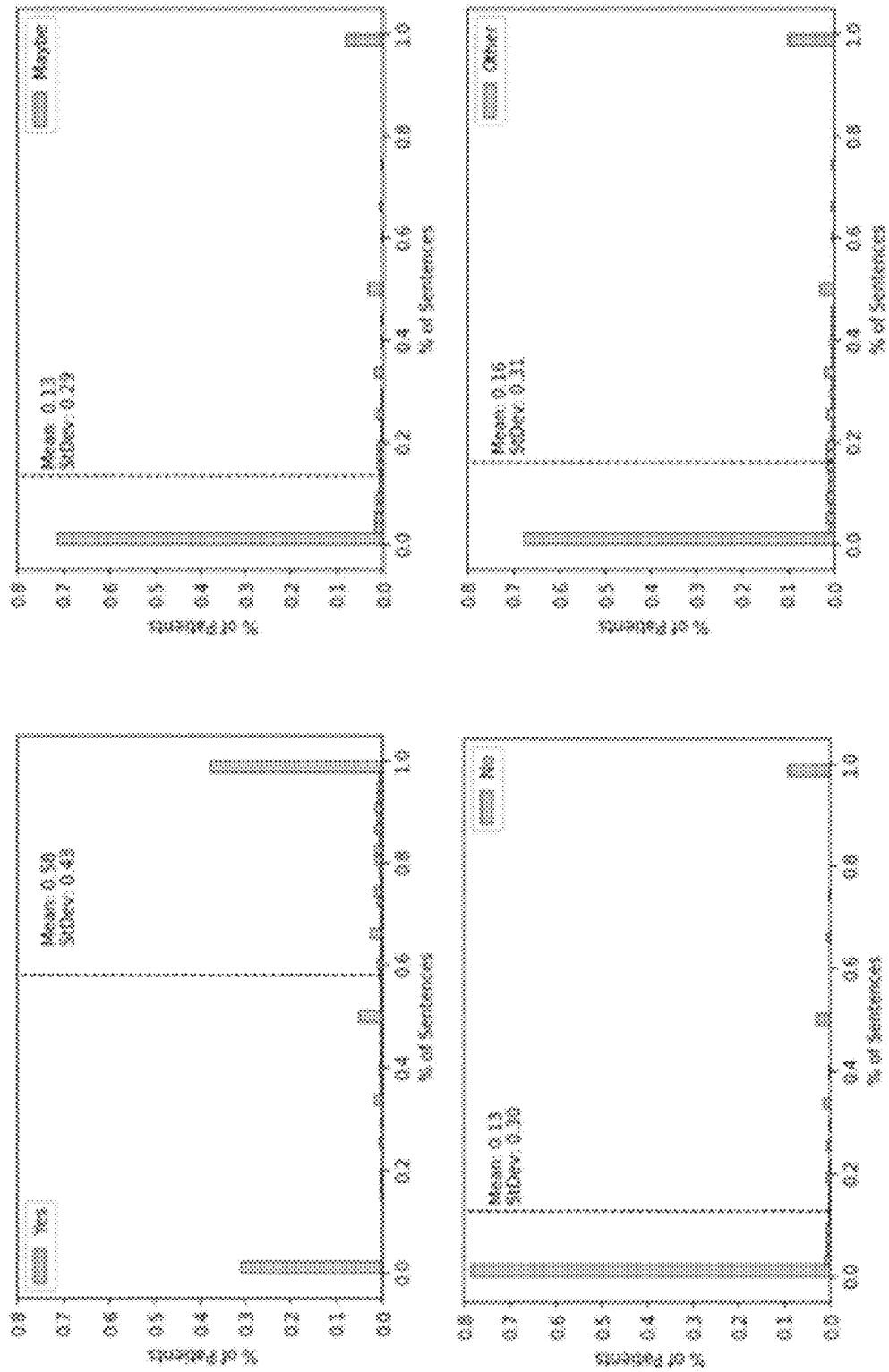
FIG. 6 represents the output from the diagnosis model in the potential PH cohort, wherein the model was run on sentences containing "pulmonary hypertension".

After validating the diagnosis model on the Mayo PH Cohort, the model was run on sentences containing "pulmonary hypertension" for the 19,504 patients in the Potential PH Cohort. As shown in FIG. 6, the average YES sentiment of 58% is lower than the Mayo PH Cohort, but this result can primarily be accounted for by the 30% of patients without a YES sentence. Similarly, almost 80% of patients do not have a sentence with NO sentiment, meaning that nference could potentially increase the PH positive control set by an order of magnitude.

To automate the differentiation between positive and negative PH patients in these cohorts, various logistic regression models were tested using a combination of augmented curation results and/or echocardiogram measurements, TRV, and estimated right atrial pressure (RAP). Features used to describe a patient via augmented curation included the percent of sentences with Yes, No, Maybe, and Other sentiment, as well as the number of PH occurrences per note. Features used for TRV and RAP included the mean, median, minimum, maximum, and standard deviation of each measurement. A positive control cohort of 1556 patients who had positive diagnoses and echocardiogram measurements was generated from the Mayo PH Cohort. A negative control cohort was generated through manual curation of records for patients with TRV and RAP measurements. Models were evaluated using 10-fold cross validation and a 90:10 train-test split.

Figure 7:
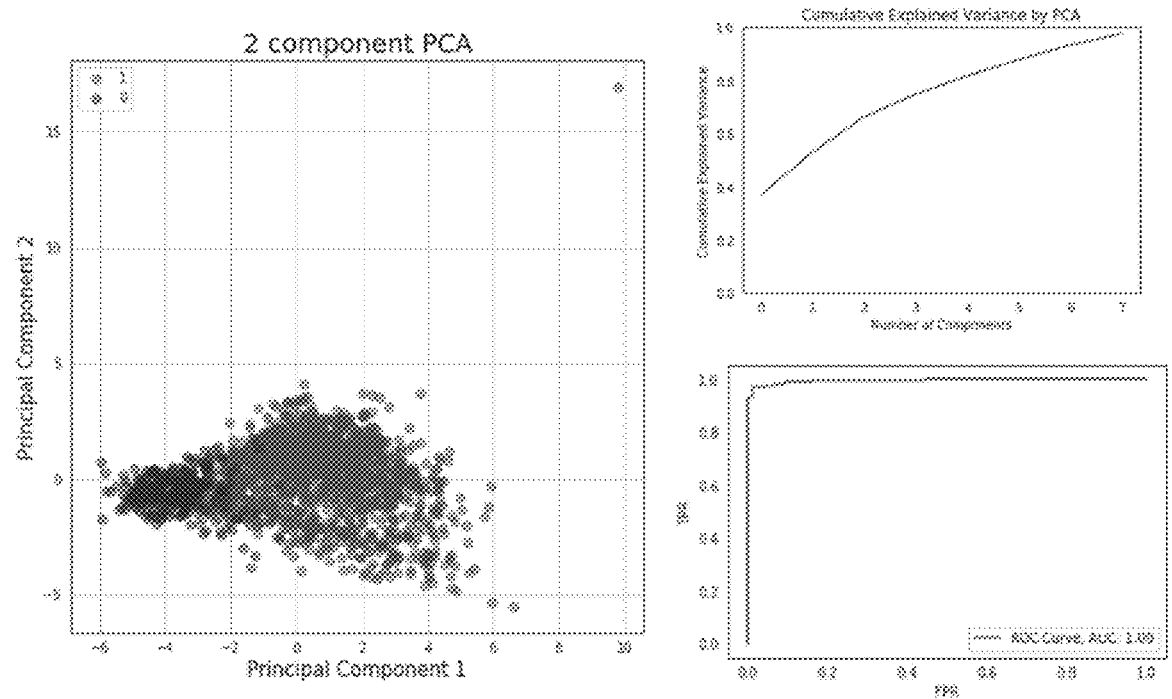
FIG. 7 represents the output from logistic regression models using a combination of augmented curation results and echocardiogram measurements.

As shown in in FIG. 7, coupling augmented curation with echocardiogram measurements performs better than either alone. Yet augmented curation performs much better than echocardiogram measurements alone. This was expected as the goal of augmented curation is to capture the physician's interpretation of the sum total of the patient's records.

Two hundred patients were randomly sampled as a hold-out set, and their records were manually curated to determine whether the patient was diagnosed with PH or not. One patient withdrew consent and was subsequently excluded. Of the remaining 199 patients, 191 were classified correctly by the logistic regression model or 95.9%.

Example 4: Algorithm Development and Results

For each cohort, preliminary models were evaluated on two different time windows: 1 month on either side of the diagnosis date (diagnosis window) and 6-18 months prior to diagnosis (pre-emptive window). For the preliminary models, all ECGs were considered for the negative patients. For the updated model, ECGs for negative patients were limited to those prior to the last procedure used to classify said patients. All ECGs taken when the patient was younger than 18 years of age were excluded. For each cohort, patients were split into train (48%), test (40%), and validation (12%) sets.

Two performance metrics were used to evaluate each model: patient-wise area under the curve (AUC) and age-gender-wise AUC. Patient-wise AUC randomly sampled one ECG per patient and the mean of 50 random runs was reported. Patient-wise AUC ensure patients with more ECGs, i.e., potentially sicker patients, are not over-represented. Age-gender-wise AUC randomly sampled 4 negative ECGs for each positive ECG matched by age and gender at the time the ECG was taken. If 4 negative ECGs are not available, positive ECGs are under-sampled to maintain a 1:4 positive-negative ECG ratio. Here again, the mean of 50 random runs is reported. The advantage here is that the age and gender distributions are maintained between the positive and negative cohorts.

Figure 10:
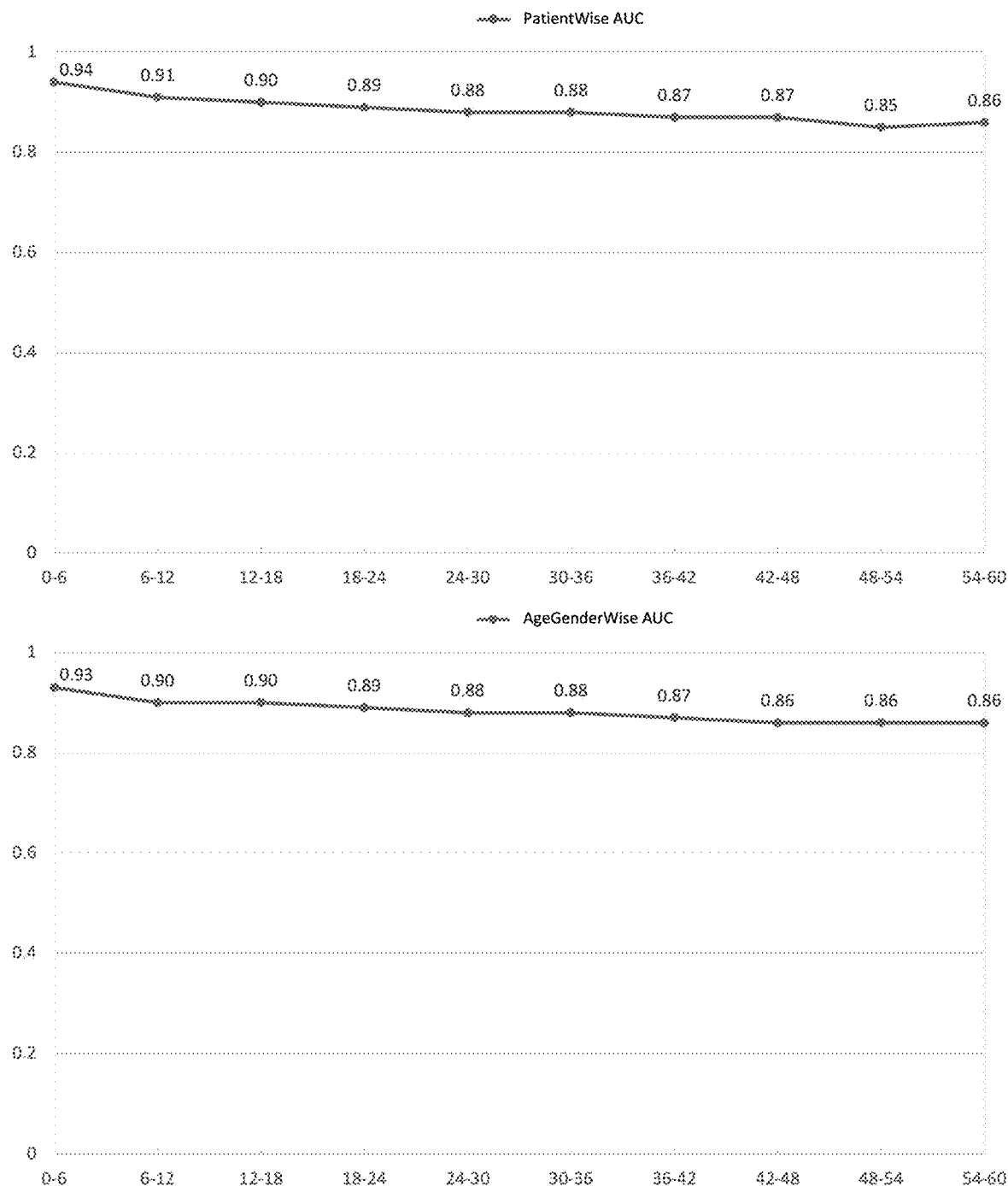
FIG. 10 depicts the Cohort 3 diagnostic model performance over time on ECGs from 6-month windows going back 5 years prior to diagnosis.

Algorithms were developed testing single-branch, four-branch, and twelve-branch 1D convolutional neural networks (CNNs), using 12-lead voltage-time signals as one input, four groups of three leads, and individual leads, respectively. Other varied parameters included age and gender as inputs, an additional 2D spectrogram, residual connections, and window size (i.e., a ten second window vs. overlapping two second windows). (see Table 4 for results from a preliminary model) An optimal model architecture was found using a single-branch 1D CNN with residual connections and overlapping two second windows (FIG. 8—shown for updated model). Age and gender were not required as inputs and inclusion of a 2D spectrogram did not dramatically increase performance (data not shown). Models were also trained using ECGs with sinus rhythm alone or by excluding patients with pacemakers, but neither modification dramatically improved performance (see Table 5 and 6 for results from a preliminary model). Finally, we tested the diagnostic model on ECGs from the pre-emptive window (FIG. 9—shown for updated model) and found that the diagnostic model performed better than the pre-emptive model for these ECGs (data not shown). The preliminary diagnostic model trained on Cohort 3 was one of the best performing models and was used for further study. We used the updated diagnostic model to test ECGs from 0-5 year prior to diagnosis in 6-month windows (FIG. 10—shown for updated model).

TABLE 4

Optimization of Model Performance (Preliminary Model Results)

| | Patient Wise AUC | | Age Gender Wise AUC | |
|---|---|---|---|---|
| Model Description | Cohort 3 | Cohort 5 | Cohort 3 | Cohort 5 |
| Optimal Model | 0.9076 | 0.8715 | 0.8947 | 0.8620 |
| Optimal Model-Residual Connections | 0.9023 | 0.8689 | 0.8918 | 0.8594 |
| Optimal Model-Residual + 12 Branch | 0.9021 | 0.8666 | 0.8907 | 0.8587 |
| Optimal Model-Residual + 10s + 12 Branch | 0.8992 | 0.8635 | 0.8881 | 0.8547 |

TABLE 5

Model AUCs for the Diagnostic Test Set Using ECGs Labeled with Sinus Rhythm Compared to All ECGs (Preliminary Model Results)

| Cohort/Set | Patient Wise AUC Mean-Sinus | Age Gender Wise AUC Mean-Sinus | Patient Wise AUC Mean-ALL | Age Gender Wise AUC Mean-ALL |
|---|---|---|---|---|
| COHORT 1: RHC ≥25 mmHg vs RHC <21 mmHg | 0.7501 | 0.7511 | 0.7613 | 0.7381 |
| COHORT 2: RHC ≥21 mmHg vs RHC <21 mmHg | 0.7352 | 0.7332 | 0.7502 | 0.7228 |
| COHORT 3: RHC ≥25 mmHg vs RHC <21 mmHg + TRV ≤2.8 m/s | 0.9034 | 0.9 | 0.9059 | 0.8935 |
| COHORT 4: RHC ≥21 mmHg vs RHC <21 mmHg + TRV ≤2.8 m/s | 0.8887 | 0.8874 | 0.8927 | 0.8828 |
| COHORT 5: TRV ≥3.4 m/s vs TRV ≤2.8 m/s | 0.8762 | 0.874 | 0.8701 | 0.8591 |
| COHORT 6: TRV ≥2.8 m/s vs TRV ≤2.8 m/s | 0.8236 | 0.8214 | 0.8193 | 0.813 |
| COHORT 8: RHC ≥25 mmHg vs RHC <21 mmHg + TRV ≤2.6 m/s | 0.9046 | 0.8967 | 0.9107 | 0.8898 |
| COHORT 9: RHC ≥21 mmHg vs RHC <21 mmHg + TRV ≤2.6 m/s | 0.8941 | 0.8867 | 0.8997 | 0.8821 |
| COHORT 10: TRV ≥3.4 m/s vs TRV ≤2.6 m/s | 0.8906 | 0.8882 | 0.8847 | 0.8729 |
| COHORT 11: TRV ≥2.8 m/s vs TRV <2.6 m/s | 0.8433 | 0.8431 | 0.8389 | 0.8347 |

TABLE 6

Model Performance When Excluding Patients With Pacemakers (Preliminary Model Results)

| | | Patientwise AUC | | Age Gender Wise AUC | |
|---|---|---|---|---|---|
| Model Trained On | Model Evaluated On | Cohort 3 | Cohort 5 | Cohort 3 | Cohort 5 |
| Full Data | Full Data | 0.9059 | 0.8701 | 0.8935 | 0.8591 |
| Full Data | On patients who never had "pacemakers" | 0.9018 | 0.8633 | 0.9005 | 0.8581 |
| Full Data | On ECGs without "pacemakers" | 0.9021 | 0.8677 | 0.8993 | 0.8619 |
| On patients who never had "pacemakers" | On patients who never had "pacemakers" | 0.8953 | 0.8632 | 0.8924 | 0.8583 |
| On ECGs without "pacemakers" | On ECGs without "pacemakers" | 0.9018 | 0.8693 | 0.8968 | 0.8632 |

Example 5: Identification of Putative Genetic Biomarkers that May Explain Early ECG Signals Related to Pulmonary Hypertension The finding that the ECG-based model for diagnosing pulmonary hypertension maintains performance in identifying pulmonary hypertension patients for up to five years prior to the diagnosis date implies that the ECG signal provides information about a patient's long-term susceptibility to pulmonary hypertension. Without wishing to be bound by theory, one possible explanation for this is that certain germline genetic mutations that predispose patients to pulmonary hypertension also modulate cardiac electrophysiology, and are therefore detectable in the ECG long before pulmonary hypertension diagnosis. The nferX® platform was employed to identify genetic mutations associated with pulmonary hypertension and subsequently triangulate evidence that supports the notion that these genes modulate ECG signals. Six candidate genes including two potassium channels, KCNK3 and KCNA5, and 4 additional genes including CAV1, SMAD4, GJB2, TBX4, were identified. (See Table 7)

associations to relevant terms associated with cardiac electrophysiology, such as "electrocardiogram", "ECG", "cardiac action potential", and "cardiac conduction". The applications nferX RNA Explorer and nferX Single Cell were used to accumulate evidence linking these genes to the heart. These genes, in addition to the potassium channel genes, may serve as a part of a gene panel of at least 10 genes that further supports the diagnosis of pulmonary hypertension given a positive ECG-based predictive test.

TABLE 7

Triangulation of molecular and literature evidence for four additional genes that have been associated with pulmonary hypertension via mutations and with the electrocardiogram via the literature.

| | nferX Human Genetics Association with PH | nferX Signals Association with ECG | nferX RNA Explorer RNA/Protein exp. in heart | nferX Single Cell RNA exp. in heart | nferX Single Cell Notable cardiac cell types with RNA exp. | nferX Single Cell Notable non-cardiac cell types with RNA exp. |
|---|---|---|---|---|---|---|
| CAV1 | Y | Y | Y/Y | Y | Endothelial cells, cardiomyocytes, smooth muscle cells | Type 1 pneumocytes |
| SMAD4 | Y | Y | Y/Y | Y | Myofibroblasts | Vascular smooth muscle, granule neurons |
| GJB2 | Y | Y | N/Y | N | | |
| TBX4 | Y | Y | N/unavailable | Y (low) | Cardiomyocytes (low) | Neurons |
| ACVRL1 | Y | Y | Y/N | Y | Endothelial cells, fibroblasts | Postcapillary venule endothelial cells |
| SMAD4 | Y | Y | Y/Y | Y (low) | Cardiomyocytes, fibroblasts, smooth muscle cells | Vascular smooth muscle cells, myofibroblasts, granule neurons |
| BMPR1A | Y | Y | Y/Y | Y (low) | Cardiomyocytes, fibroblasts, smooth muscle cells, endothelial cells, immune cells | Type 1 pneumocytes, lung epithelial precursors |
| BMPR2 | Y | Y | Y/Y | Y (low) | Endothelial cells, cardiomyocytes, fibroblasts | Type 1 pneumocytes, endothelial cells |

Figure 11:
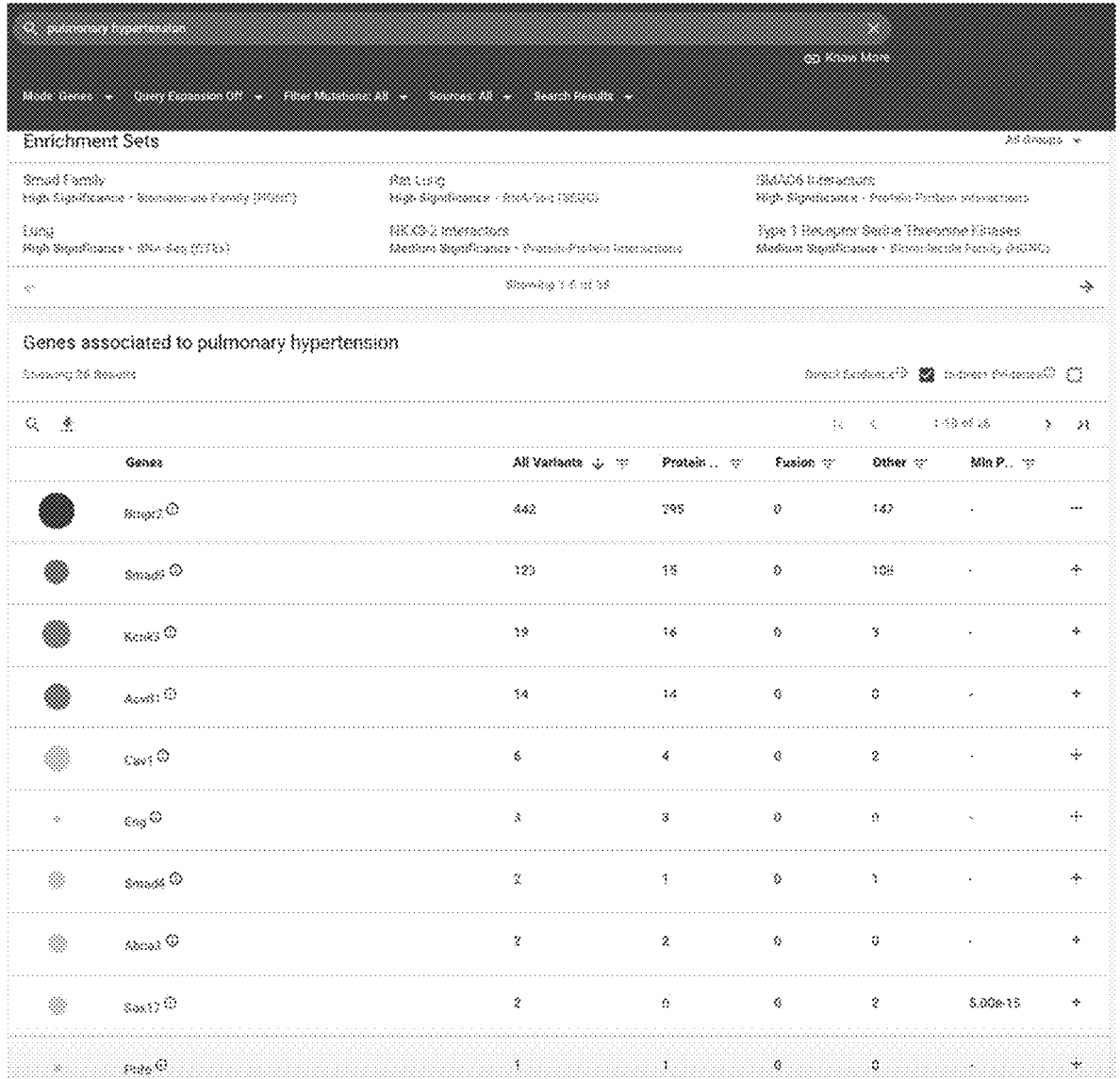
FIG. 11 presents the output of the nferX® Human Genetics application, which identified 26 genes in which mutations have been associated with pulmonary hypertension. Two of these, KCNK3 and KCNA5, are potassium channels.
Figure 12A:
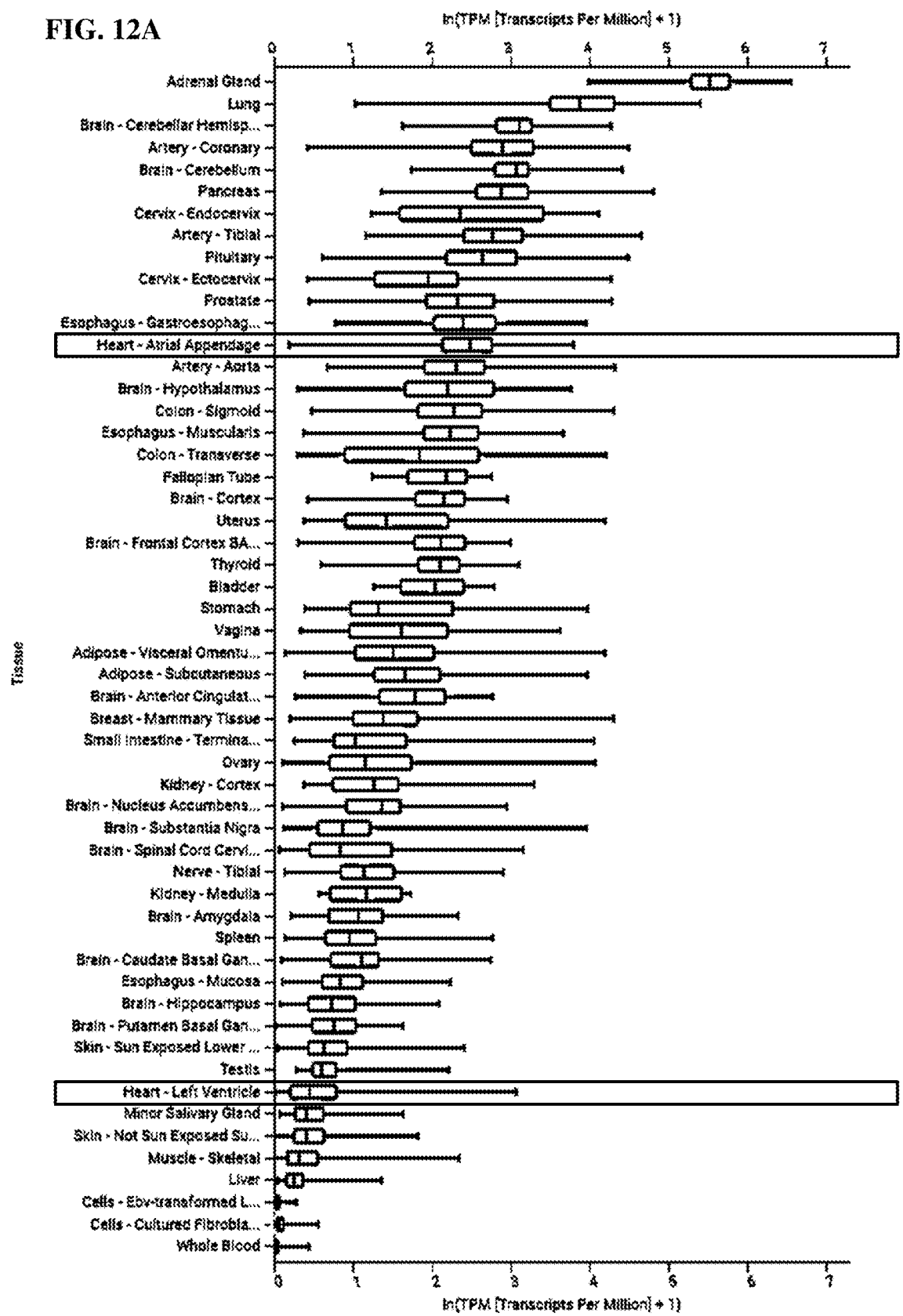
FIG. 12A-B presents the output of the nferX® RNA Explorer application, which demonstrated that expression of both KCNK3 (A, lower) and KCNA5 (B, lower) is observed in heart tissue as well as neuronal tissue.
Figure 12B:
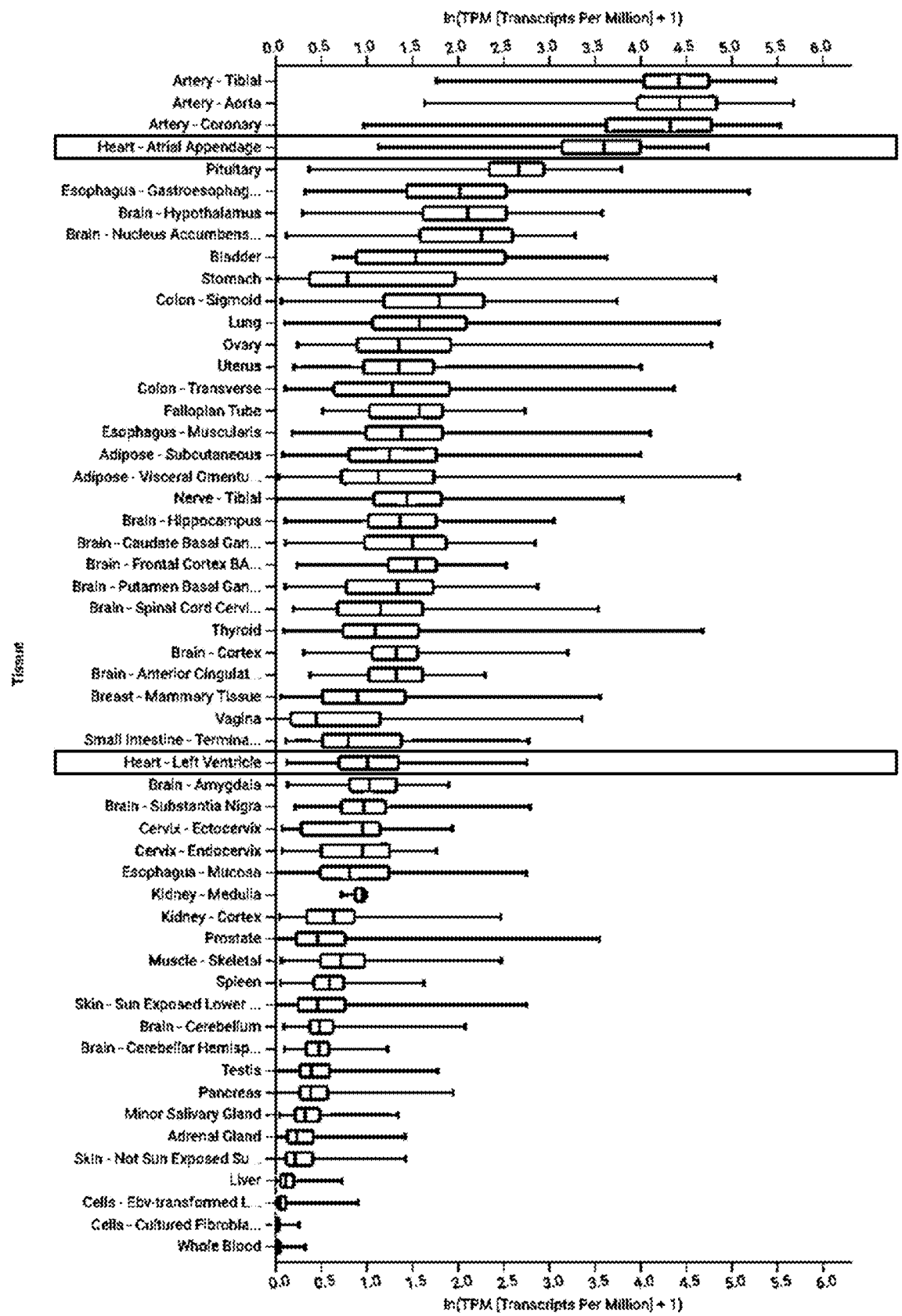
Figure 14:
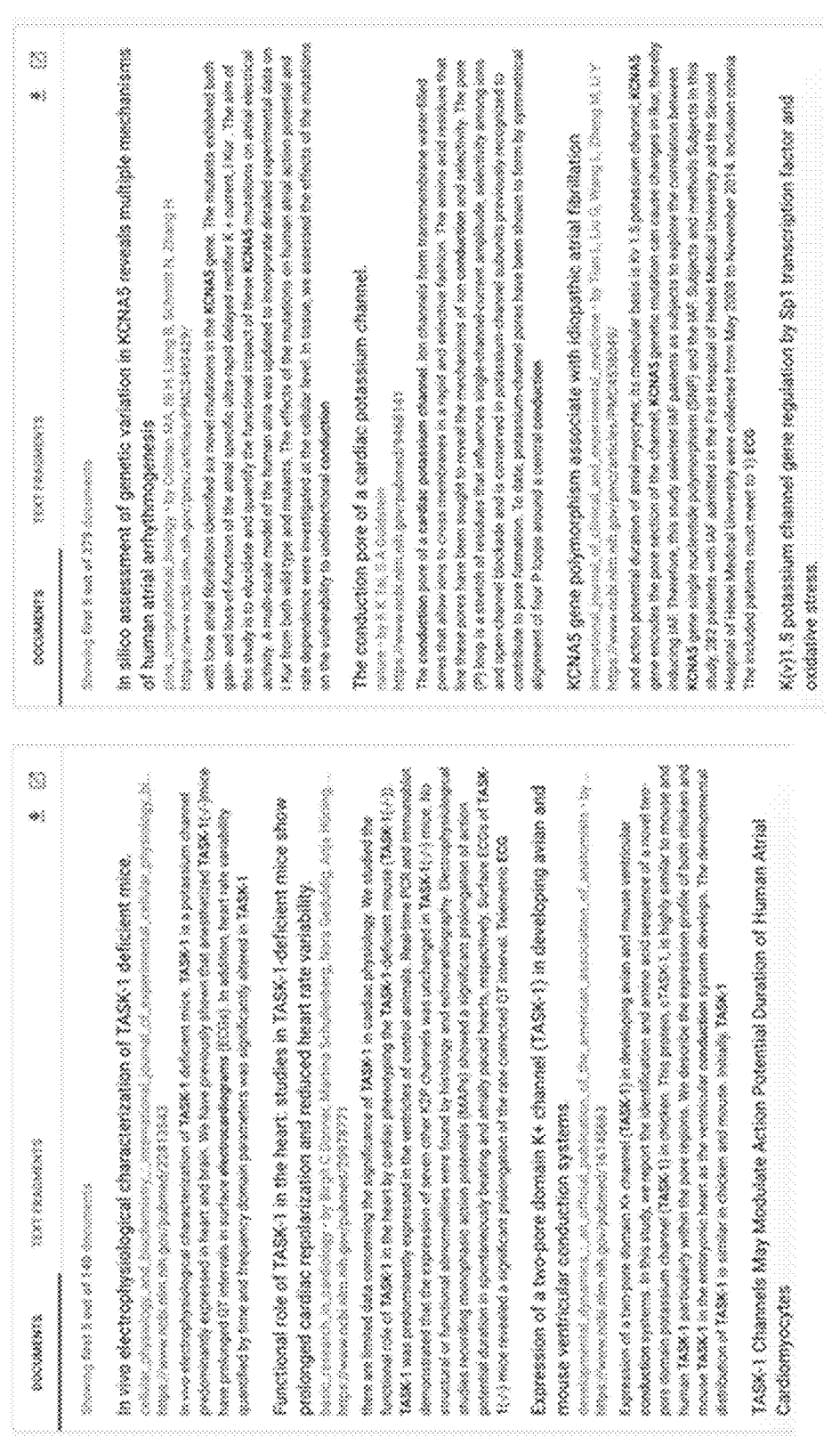

The nferX Human Genetics application reveals that 26 genes have been associated with pulmonary hypertension (FIG. 11). Of these genes, two, KCNK3 and KCNA5, are potassium channels that are expressed in cardiac tissue (FIG. 12). We prioritized KCNK3 and KNCA5 for further investigation because potassium channels are known contributors to cellular action potentials; the cardiac action potential is the basis of the signal observed by the ECG. The nferX Single Cell application demonstrates that, at the single cell level, KCNK3 and KCNA5 are expressed strongly in neuronal and cardiac cell types, respectively (FIG. 13). At lower expression levels, KNCK3 expression is also observed in cardiac cell types (not shown). Finally, The nferX Signals application identifies literature evidence that both KCNK3 and KCNA5 impact cardiac electrophysiology (FIG. 14).

Figure 15:
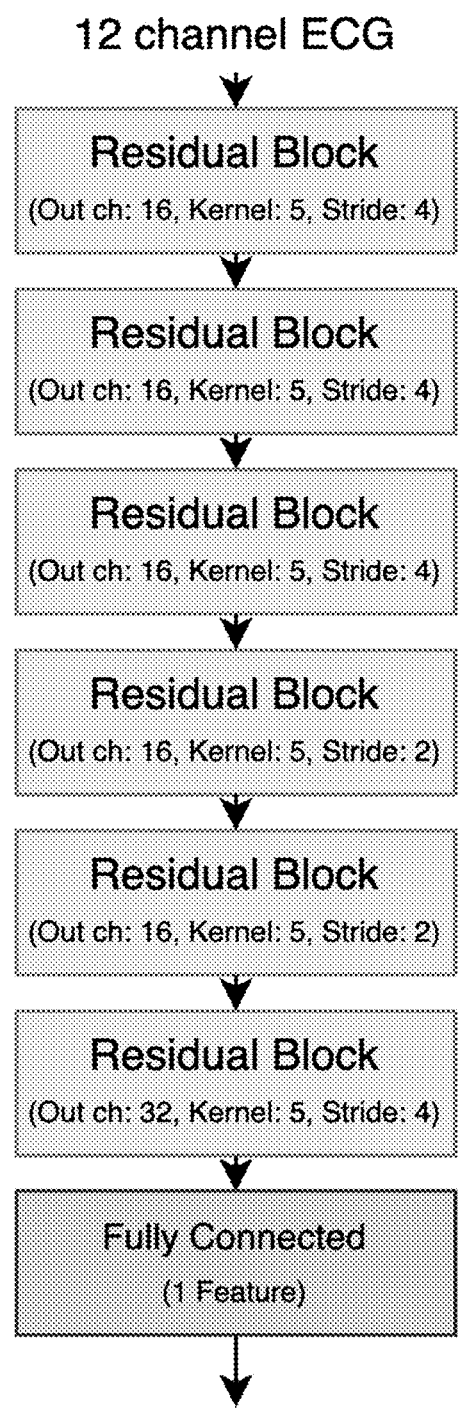
FIG. 15 depicts a network architecture diagram for an exemplary seven-layer convolutional neural network CNN model, without transformer layers.

We further investigated the non-ion channel genes that were identified by nferX Human Genetics as containing mutations that are associated with pulmonary hypertension. Eight of these genes, CAV1, SMAD4, GJB2, ACVRL1, SMAD4, BMPR1A, BMPR2, and TBX4, have prominent Example 6: TimeSeriesConvolution Neural Network Architecture without Transformer Layers A seven-layer 'ConvolutionTransformer' neural network architecture was designed, which receives a 12-channel ECG and outputs an indication of the presence of pulmonary hypertension as set forth above. (See FIG. 15).

Figure 16:
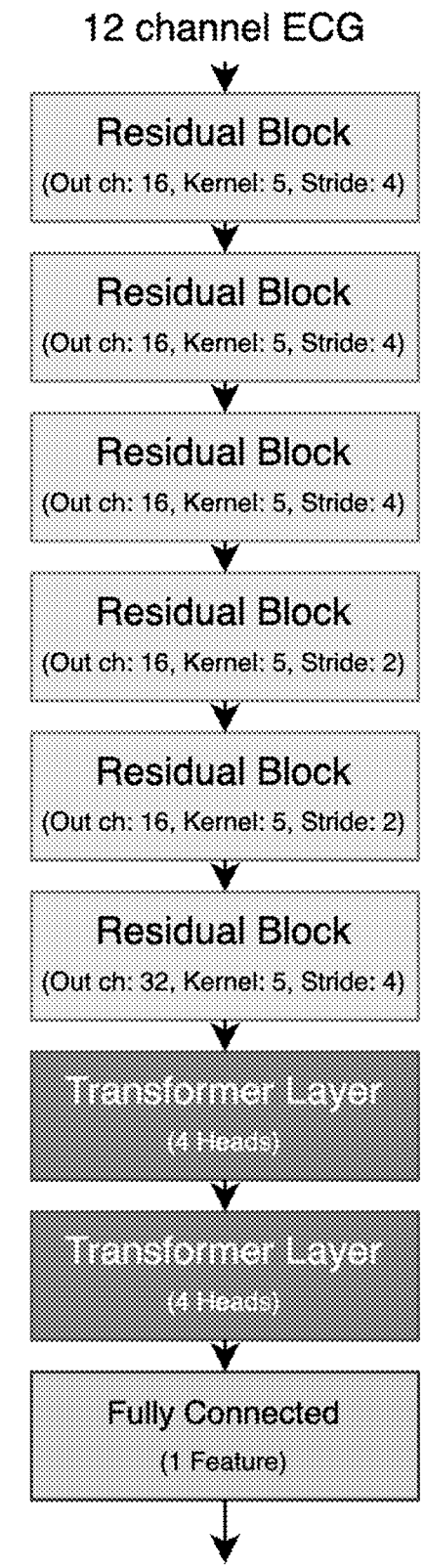
FIG. 16 depicts a network architecture diagram for an exemplary nine-layer convolutional neural network (CNN) model, comprising two transformer layers.
Figure 17A:
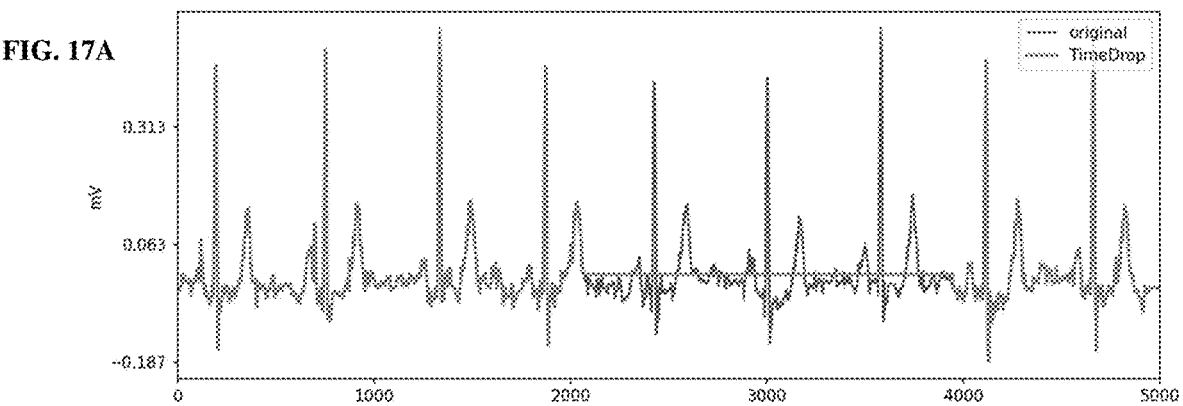
FIG. 17A-E depicts the data augmentation in the training set to ensure that neural networks are less prone to overfitting. Said data is augmented by randomly applying one of (A) masking a portion of time in the whole signal; (B) Allowing only frequencies between 0.5 to 50 Hz; (C) Stretching the signal with some zoom level; (D) Shifting voltages in different leads by a small voltage; (E) Dropping of a frequency band with 1 and 50 Hz; or shuffling a small set of leads.
Figure 17B:
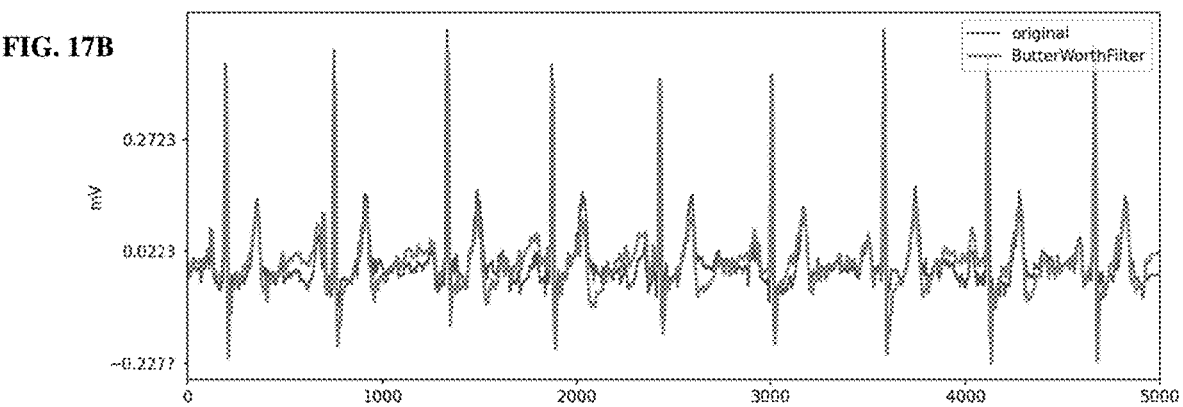
Figure 17C:
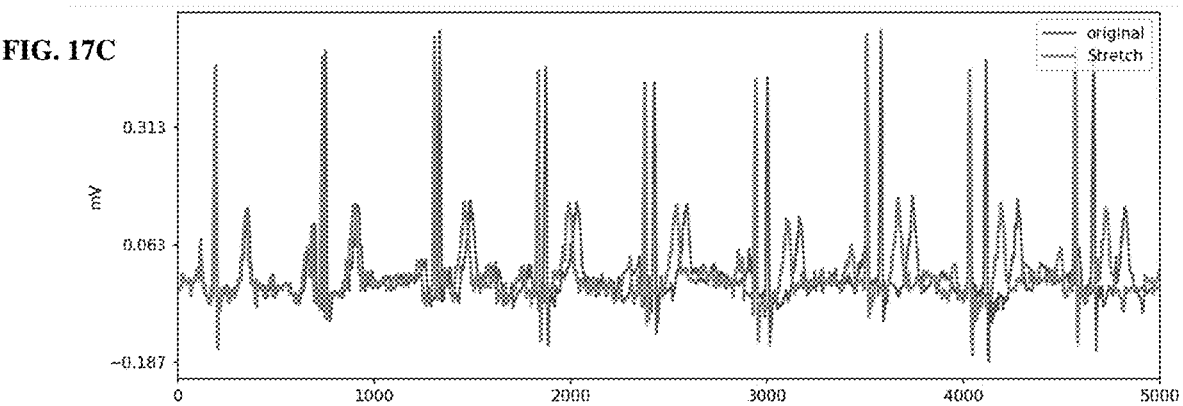
Figure 17D:
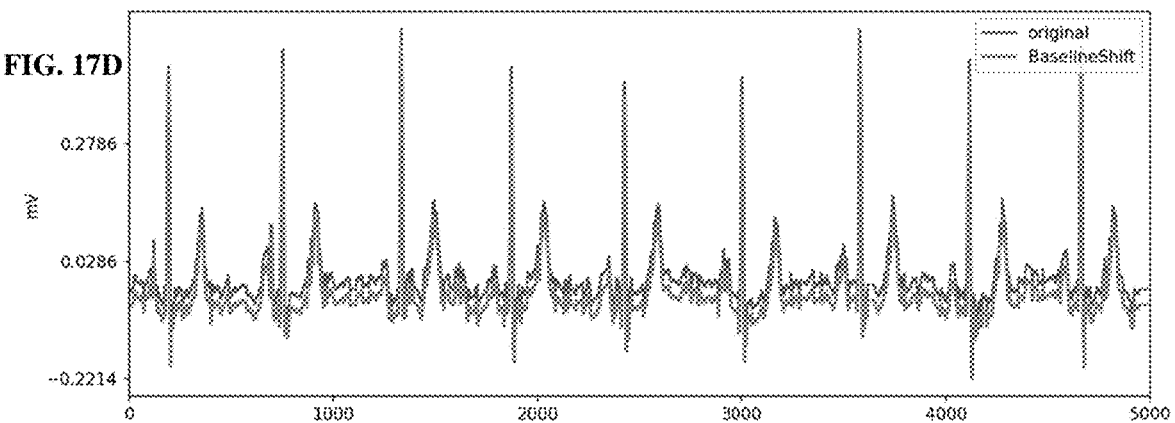
Figure 17E:
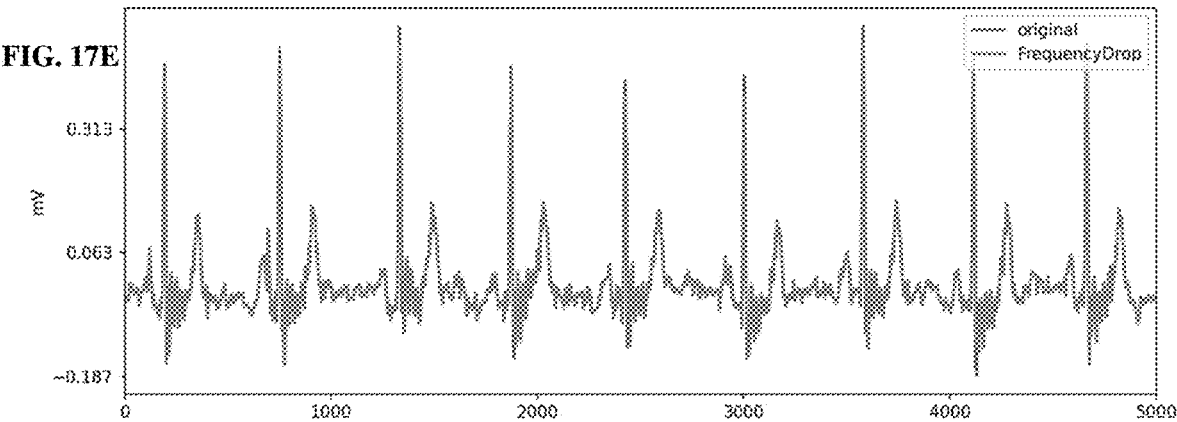

Example 7: 'ConvolutionTransformer' Neural Network Architecture with Transformer Layers In order to increase interactions across different portions of the ECG signal compared to the TimeSeriesConvolution model of Example 6, an alternative neural network architecture referred to as 'ConvolutionTransformer' is provided. It employed convolutional neural networks to generate fixed size encoding for smaller portions of ECG waveforms. A sequence of such generated encodings is passed to a Transformer network to generate the predictions as illustrated in the network architecture diagram of FIG. 16. The use of 5 second crops instead of 2 second crops enabled these longer interactions.

Example 8: Data Augmentation

Data augmentation during the training phase was used to reduce the susceptibility of the neural network to overfitting. The training data set was augmented by randomly applying one of the parameters A-F below, with 40% probability during the training alone. See also FIG. 17(A-E).
A. Masking a portion of time in the whole signal
B. Allowing only frequencies between 0.5 to 50 Hz
C. Stretching the signal with some zoom level
D. Shifting voltages in different leads by a small voltage
E. Dropping of a frequency band with 1 and 50 Hz
F. Shuffling a small set of leads Results of augmentation testing for the CNN with and without transformer layers are presented in Table 8.

TABLE 8

Augmentation Testing Results

| Augmentation Type | CONV. TRANSFORMER | | CONVOLUTION | |
| --- | --- | --- | --- | --- |
| | Patient AUC | AgeGender AUC | Patient AUC | AgeGender AUC |
| No Augmentations | 0.9691 | 0.9677 | 0.9468 | 0.9439 |
| Baseline Shift | 0.9785 | 0.9763 | 0.9473 | 0.9441 |
| ButterWorth Filter | 0.9766 | 0.9741 | 0.9471 | 0.9442 |
| Channel Shift | 0.9764 | 0.9739 | 0.9459 | 0.9433 |
| Frequency Drop | 0.9782 | 0.9753 | 0.9462 | 0.9433 |
| Stretch | 0.9828 | 0.9806 | 0.9468 | 0.9441 |
| Time Drop | 0.9706 | 0.9677 | 0.9465 | 0.9437 |

All publications (including patents, patent applications and sequence accession numbers mentioned herein) are hereby incorporated by reference in their entirety as if each individual publication was specifically and individually indicated to be incorporated by reference. In case of conflict, the present application, including any definitions herein, will control.

Those skilled in the art will recognize, or be able to ascertain using no more than routine experimentation, many equivalents to the specific embodiments of the invention described herein. Such equivalents are intended to be encompassed by the following claims.

What is claimed is:

1. A method comprising:
   receiving voltage-time data of a subject, the voltage-time data comprising an electrocardiogram (ECG) waveform of a plurality of leads of an electrocardiograph;
   generating a plurality of feature vectors from the voltage-time data, wherein each of the feature vectors comprises a portion of the ECG waveform;
   providing the plurality of the feature vectors to a pretrained learning system, wherein the pretrained learning system comprises:
      a machine-learning model configured to:
         generate a plurality of fixed size encodings from the plurality of feature vectors respectively; and
         generate predictions based on the plurality of fixed size encodings;
      receiving from the pretrained learning system an indication of a presence or absence of pulmonary hypertension in the subject based on the predictions; and
      providing the indication to a computing node for display to a user.

2. The method of claim 1, wherein generating the feature vectors comprises at least one of generating a spectrogram based on voltage data of the plurality of leads, and grouping the voltage data of the plurality of leads into a plurality of subsets.

3. The method of claim 1, further comprising at least one of:
   receiving demographic information of the subject, wherein generating the feature vectors comprises adding the demographic information to the feature vectors; and
   receiving genomic information of the subject, wherein generating the feature vectors comprises adding the genomic information to the feature vectors.

4. The method of claim 1, wherein the pretrained learning system comprises a convolutional neural network that comprises at least one residual connection.

5. The method of claim 1, wherein the voltage-time data of a subject is received from at least one of an electrocardiograph and an electronic medical record.

6. The method of claim 1, further comprising: providing the indication to an electronic health record system for storage in a health record associated with the subject.

7. A system comprising:
   an electrocardiograph comprising a plurality of leads;
   a computing node, operating a on a processor, comprising a non-transitory computer readable storage medium having program instructions embodied therewith, the program instructions executable by the processor of the computing node to cause the processor to perform a method comprising:
      receiving voltage-time data of a subject from voltage-time data comprising electrocardiogram (ECG) waveform of the plurality of leads;
      generating a plurality of feature vectors from 8the voltage-time data, wherein each of the feature vectors comprises a portion of the ECG waveform;
      providing the plurality of feature vectors to a pretrained learning system, wherein the pretrained learning system comprises:
         a machine learning model configured to:
            generate a plurality of fixed size encodings from the plurality of feature vectors respectively; and
            generate predictions based on the plurality of fixed size encodings;
         receiving from the pretrained learning system an indication of presence or absence of pulmonary hypertension in the subject based on the predictions; and
         providing the indication to a computing node for display to a user.

8. The system of claim 7, wherein generating the feature vectors comprises at least one of generating a spectrogram based on the voltage time data of the plurality of leads, and grouping the voltage data of the plurality of leads into a plurality of subsets.

9. The system of claim 7, further comprising at least one of:
   receiving demographic information of the subject, wherein generating the feature vectors comprises adding the demographic information to the feature vectors, and
   receiving genomic information of the subject, wherein generating the feature vectors comprises adding the genomic information to the feature vectors.

10. The system of claim 7, wherein the pretrained learning system comprises a convolutional neural network that comprises at least one residual connection.

11. The system of claim 7, wherein the voltage-time data of a subject is received from at least one of an electrocardiograph and an electronic medical record.

12. The system of claim 7, further comprising providing the indication to an electronic health record system for storage in a health record associated with the subject.

13. A computer program product for detection of pulmonary hypertension, the computer program product comprising a non-transitory computer readable storage medium having program instructions embodied therewith, the program instructions executable by a processor to cause the processor to perform a method comprising:
 receiving voltage-time data of a subject from voltage-time data comprising electrocardiogram (ECG) waveform of a plurality of leads;
 generating a plurality of feature vectors from the voltage-time data, wherein each of the feature vectors comprises a portion of the ECG waveform;
 providing the plurality of feature vectors to a pretrained learning system, wherein the pretrained learning system comprises:
  a machine learning model configured to:
   generate a plurality of fixed size encodings from the plurality of feature vectors respectively; and generate predictions based on the plurality of fixed size encodings;
 receiving from the pretrained learning system an indication of a presence or absence of pulmonary hypertension in the subject based on the predictions; and
 providing the indication to a computing node for display to a user.

14. The computer program product of claim 13, wherein generating the feature vectors comprises at least one of generating a spectrogram based on the voltage-time data of the plurality of leads, and grouping the voltage data of the plurality of leads into a plurality of subsets.

15. The computer program product of claim 13, further comprising at least one of:
 receiving demographic information of the subject, wherein generating the feature vectors comprises adding the demographic information to the feature vectors; and
 receiving genomic information of the subject, wherein generating the feature vectors comprises adding the genomic information to the feature vectors.

16. The computer program product of claim 13, wherein the pretrained learning system comprises a convolutional neural network that comprises at least one residual connection.

17. The computer program product of claim 13, wherein the voltage-time data of a subject is received from at least one of an electrocardiograph and an electronic medical record.

18. The computer program product of claim 13, further comprising:
 providing the indication to an electronic health record system for storage in a health record associated with the subject.

* * * * *